(12) United States Patent
Jollota

(10) Patent No.: US 8,755,269 B2
(45) Date of Patent: Jun. 17, 2014

(54) RANKING AND SWITCHING OF WIRELESS CHANNELS IN A BODY AREA NETWORK OF MEDICAL DEVICES

(75) Inventor: James Jollota, Simi Valley, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 1003 days.

(21) Appl. No.: 12/646,754

(22) Filed: Dec. 23, 2009

(65) Prior Publication Data

US 2011/0149759 A1 Jun. 23, 2011

(51) Int. Cl.
G01R 31/08 (2006.01)

(52) U.S. Cl.
USPC ........... 370/225; 370/242; 370/248; 370/332; 370/437

(58) Field of Classification Search
USPC ......... 370/216, 225–228, 241, 242, 245, 248, 370/252, 329, 332, 333, 338, 348, 431, 433, 370/437
See application file for complete search history.

(56) References Cited

U.S. PATENT DOCUMENTS

| | | |
|---|---|---|
| 3,631,847 A | 1/1972 | Hobbs, II |
| 4,212,738 A | 7/1980 | Henne |
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |

(Continued)

FOREIGN PATENT DOCUMENTS

| | | |
|---|---|---|
| DE | 4329229 | 3/1995 |
| EP | 0319268 | 11/1988 |

(Continued)

OTHER PUBLICATIONS

PCT Search Report (PCT/US02/03299), Oct. 31, 2002, Medtronic Minimed, Inc.

(Continued)

*Primary Examiner* — Yemane Mesfin
*Assistant Examiner* — Mon Cheri Davenport
(74) *Attorney, Agent, or Firm* — Ingrassia Fisher & Lorenz, P.C.

(57) ABSTRACT

Operating techniques and methodologies for a body area network of medical devices are provided. One technique relates to an intelligent channel hopping scheme that detects loss of wireless synchronization on an initial wireless channel, thereafter obtains a measure of quality for the initial wireless channel, and then selects a new wireless channel when the obtained measure of quality fails to satisfy a threshold criteria. Another operating technique dynamically adapts an ordered list of available wireless channels in accordance with a quality measure of the available wireless channels. Thus, when quality degradation associated with a first wireless channel is detected, the ordered list can be updated to indicate a lower preference for the first wireless channel and to indicate a higher preference for a second wireless channel that does not suffer from quality degradation. Another channel hopping or switching technique selects wireless channels in a manner that is influenced by the current geographic position of the medical device.

13 Claims, 8 Drawing Sheets

(56) References Cited

U.S. PATENT DOCUMENTS

| | | |
|---|---|---|
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,497,772 A | 3/1996 | Schulman et al. |
| 5,505,709 A | 4/1996 | Funderburk et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,167,260 A * | 12/2000 | Azam et al. .................. 455/434 |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |

(56) References Cited

U.S. PATENT DOCUMENTS

| | | |
|---|---|---|
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0203824 A1 | 10/2004 | Mock et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0055244 A1* | 3/2005 | Mullan et al. ............... 705/2 |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0115846 A1* | 5/2007 | Kooyers et al. ............ 370/252 |
| 2007/0135866 A1 | 6/2007 | Baker et al. |
| 2008/0154503 A1 | 6/2008 | Wittenber et al. |
| 2009/0081951 A1 | 3/2009 | Erdmann et al. |
| 2009/0082635 A1 | 3/2009 | Baldus et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |

OTHER PUBLICATIONS (Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting a Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

Hirsch I B et al. (1990). Intensive Insulin Therapy for Treatment of Type I Diabetes. Diabetes Care, vol. 13, No. 12, pp. 1265-1283.

Kulkarni K et al. (1999). Carbohydrate Counting a Primer for Insulin Pump Users to Zero in on Good Control. MiniMed Inc.

Marcus A O et al. (1996). Insulin Pump Therapy Acceptable Alternative to Injection Therapy. Postgraduate Medicine, vol. 99, No. 3, pp. 125-142.

Reed J et al. (1996). Voice of the Diabetic, vol. 11, No. 3, pp. 1-38.

Skyler J S (1989). Continuous Subcutaneous Insulin Infusion [CSII] With External Devices: Current Status. Update in Drug Delivery Systems, Chapter 13, pp. 163-183. Futura Publishing Company.

Skyler J S et al. (1995). The Insulin Pump Therapy Book Insights from the Experts. MiniMed•Technologies.

Strowig S M (1993). Initiation and Management of Insulin Pump Therapy. The Diabetes Educator, vol. 19, No. 1, pp. 50-60.

Walsh J, et al. (1989). Pumping Insulin: The Art of Using an Insulin Pump. Published by MiniMed• Technologies.

(Intensive Diabetes Management, 1995). Insulin Infusion Pump Therapy. pp. 66-78.

Disetronic My Choicer™ D-TRON™ Insulin Pump Reference Manual. (no date).

Disetronic H-TRON® plus Quick Start Manual. (no date).

Disetronic My Choice H-TRONplus Insulin Pump Reference Manual. (no date).

Disetronic H-TRON© plus Reference Manual. (no date).

(MiniMed, 1996). The MiniMed 506. 7 pages. Retrieved on Sep. 16, 2003 from the World Wide Web: http://web.archive.org/web/19961111054527/www.minimed.com/files/506_pic.htm.

(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.

(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.

(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.

(56) References Cited

OTHER PUBLICATIONS (MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump a Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequisite of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.
Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172.
Nishida, Kenro, et al., "Clinical applications of teh wearable artifical endocrine pancreas with the newly designed needle-type glucose sensor," Elsevier Sciences B.V., 1994, pp. 353-358.
Nishida, Kenro, et al., "Development of a ferrocene-mediated needle-type glucose sensor covereed with newly designd biocompatible membrane, 2-methacryloyloxyethylphosphorylcholine -co-n-butyl nethacrylate," Medical Progress Through Technology, vol. 21, 1995, pp. 91-103.
Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.
Reach, G., "A Method for Evaluating in vivo the Functional Characteristics of Glucose Sensors," Biosensors 2, 1986, pp. 211-220.
Shaw, G. W., et al., "In vitro testing of a simply constructed, highly stable glucose sensor suitable for implantation in diabetic patients," Biosensors & Bioelectronics 6, 1991, pp. 401-406.
Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.
Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.
Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.
Shichiri, Motoaki, et al., "Glycaemic Control in a Pacreatectomized Dogs with a Wearable Artificial Endocrine Pancreas," Diabetologia, vol. 24, 1983, pp. 179-184.
Shichiri, M., et al., "In Vivo Characteristics of Needle-Type Glucose Sensor—Measurements of Subcutaneous Glucose Concentrations in

(56) References Cited

OTHER PUBLICATIONS

Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

* cited by examiner

RANKING AND SWITCHING OF WIRELESS CHANNELS IN A BODY AREA NETWORK OF MEDICAL DEVICES

TECHNICAL FIELD

Embodiments of the subject matter described herein relate generally to wireless communication and wireless systems. More particularly, embodiments of the subject matter relate to channel hopping or switching techniques suitable for use in a body area (or personal area) network, such as a medical device network that includes wireless devices.

BACKGROUND

Wireless devices and related wireless communication techniques and protocols have become ubiquitous in modern society. Indeed, the prior art is replete with wireless devices such as cellular telephones, mobile computers, personal digital assistants, digital media players, portable video game devices, and the like. Moreover, portable medical devices having wireless data communication capabilities are becoming increasingly popular, especially for patients that have conditions that must be monitored on a continuous or frequent basis. For example, diabetics are usually required to modify and monitor their daily lifestyle to keep their body in balance, in particular, their blood glucose ("BG") levels. Individuals with Type 1 diabetes and some individuals with Type 2 diabetes use insulin to control their BG levels. To do so, diabetics routinely keep strict schedules, including ingesting timely nutritious meals, partaking in exercise, monitoring BG levels daily, and adjusting and administering insulin dosages accordingly. Diabetics may utilize wireless medical devices that are deployed in a network environment in a manner that facilitates data communication between two or more separate devices.

The prior art includes a number of insulin pump systems that are designed to deliver accurate and measured doses of insulin via infusion sets (an infusion set delivers the insulin through a small diameter tube that terminates at a cannula inserted under the patient's skin). In lieu of a syringe, the patient can simply activate the insulin pump to administer an insulin bolus as needed, for example, in response to the patient's current BG level. A patient can measure his BG level using a BG measurement device, such as a test strip meter, a continuous glucose measurement system, or the like. BG measurement devices use various methods to measure the BG level of a patient, such as a sample of the patient's blood, a sensor in contact with a bodily fluid, an optical sensor, an enzymatic sensor, or a fluorescent sensor. When the BG measurement device has generated a BG measurement, the measurement is displayed on the BG measurement device. A continuous glucose monitoring system can monitor the patient's BG level in real time.

Insulin pumps and continuous glucose monitoring devices may also be configured to communicate with remote control devices, monitoring or display devices, BG meters, and other devices associated with such an infusion system. For example, a continuous glucose monitoring sensor may include a wireless radio frequency ("RF") transmitter that communicates with a BG monitor device within the infusion system. As another example, the infusion system may include a handheld remote control that communicates with the infusion pump device using wireless techniques.

BRIEF SUMMARY

An exemplary embodiment of a method of operating a wireless coordinator device in a body area network of wireless medical devices is provided. The method detects loss of wireless synchronization, for a current wireless data communication channel, between the wireless coordinator device and a wireless end node device of the body area network of medical devices. In response to detecting loss of wireless synchronization, the process obtains a measure of quality for the current wireless data communication channel. When the obtained measure of quality fails to satisfy a threshold criteria, a new wireless data communication channel is selected for the wireless coordinator device. Then, wireless beacons are transmitted with the wireless coordinator device, using the new wireless data communication channel.

Also provided is an exemplary embodiment of a method of operating a wireless coordinator device in a wireless network that includes a wireless end node device. This method involves obtaining, at the wireless coordinator device, a ping schedule for the wireless end node device. The ping schedule indicates time slots during which the wireless coordinator device should expect to receive pings from the wireless end node device. The process continues by configuring the wireless coordinator device to monitor for pings sent by the wireless end node device in accordance with the ping schedule. The wireless coordinator device performs wireless data communication with the wireless end node device, using a current wireless data communication channel. The process also detects that the wireless coordinator device missed a number of expected pings as indicated by the ping schedule. In response to the detecting step, quality of the current wireless data communication channel is tested. When the quality of the current wireless data communication channel is below a threshold quality measure, the process selects a new wireless data communication channel and, thereafter, the wireless coordinator device uses the new wireless data communication channel to transmit wireless beacons.

An exemplary embodiment of a wireless medical device for a body area network of medical devices is also provided. The wireless medical device includes: a processor; a memory element coupled to the processor and configured to store a ping schedule for a wireless end node device; and a wireless communication module coupled to the processor and configured to receive ping messages from the wireless end node device using a current wireless data communication channel. The processor is configured to: detect when the wireless communication module has missed a number of expected pings from the wireless end node device, as indicated by the ping schedule; test a quality characteristic of the current wireless data communication channel when the wireless communication module has missed the number of expected pings; and switch from the current wireless data communication channel to a new wireless data communication channel when the quality characteristic fails to satisfy predetermined quality criteria.

Also provided is an exemplary embodiment of a method of operating a wireless coordinator device in a wireless network that includes at least one wireless end node device. This method maintains, at the wireless coordinator device, an ordered list of available wireless channels for wireless data communication between the wireless coordinator device and the at least one wireless end node device, wherein the ordered list is arranged in accordance with a quality measure of the available wireless channels, and wherein the ordered list includes an entry for a first wireless channel utilized by the wireless coordinator device. The method continues by detecting quality degradation associated with the first wireless channel. In response to detecting the quality degradation, the process tests a quality characteristic of a second wireless channel in the ordered list. When the quality characteristic satisfies a quality criteria for the wireless coordinator device, the process updates the ordered list of available wireless channels to indicate a higher preference for the second wireless channel and a lower preference for the first wireless channel.

Also provided is an exemplary embodiment of a method of operating a wireless device in a wireless network having a wireless coordinator device. This method receives, from the wireless coordinator device in the wireless network, an initial ordered list of available wireless channels for wireless data communication between the wireless device and the wireless coordinator device, wherein the ordered list is arranged in accordance with a quality measure of the available wireless channels, and wherein the ordered list includes an entry for a first wireless channel. The method involves wireless communication with the wireless coordinator device, using the first wireless channel. The method continues by determining that wireless connectivity with the wireless coordinator device has been lost, and, in response to the determining step, searching for wireless beacons sent by the wireless coordinator device using the available wireless channels, other than the first wireless channel, wherein the searching step traverses the available wireless channels sequentially in accordance with the ordered list.

An exemplary embodiment of a wireless coordinator device for a network of wireless devices is also provided. The wireless coordinator device includes: a processor; a memory element coupled to the processor and configured to store a list of available wireless channels, wherein the list is ordered in accordance with interference or noise associated with the available wireless channels; and a wireless communication module coupled to the processor and configured to send the list of available wireless channels to a wireless end node device in the network, using a first wireless channel. The processor is configured to detect quality degradation associated with the first wireless channel and, in response thereto, reorder the list of available wireless channels. The wireless communication module is configured to send the reordered list of available wireless channels to the wireless end node device.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

For the sake of brevity, conventional techniques related to wireless devices, wireless data communication, medical devices, infusion system operation, insulin pump operation, blood glucose sensing and monitoring, and other functional aspects of the systems (and the individual operating components of the systems) may not be described in detail here. Exemplary embodiments are described herein in the context of an insulin infusion system having wireless medical devices. Examples of infusion pumps and/or communication options may be of the type described in, but not limited to, U.S. Pat. Nos. 4,562,751; 4,685,903; 5,080,653; 5,505,709; 5,097,122; 6,554,798; 6,558,320; 6,558,351; 6,641,533; 6,659,980; 6,752,787; 6,817,990; and 6,932,584, which are herein incorporated by reference. Examples of glucose sensing and/or monitoring devices may be be of the type described in, but not limited to, U.S. Pat. Nos. 6,484,045; 6,809,653; 6,892,085; and 6,895,263, which are herein incorporated by reference.

Figure 1:
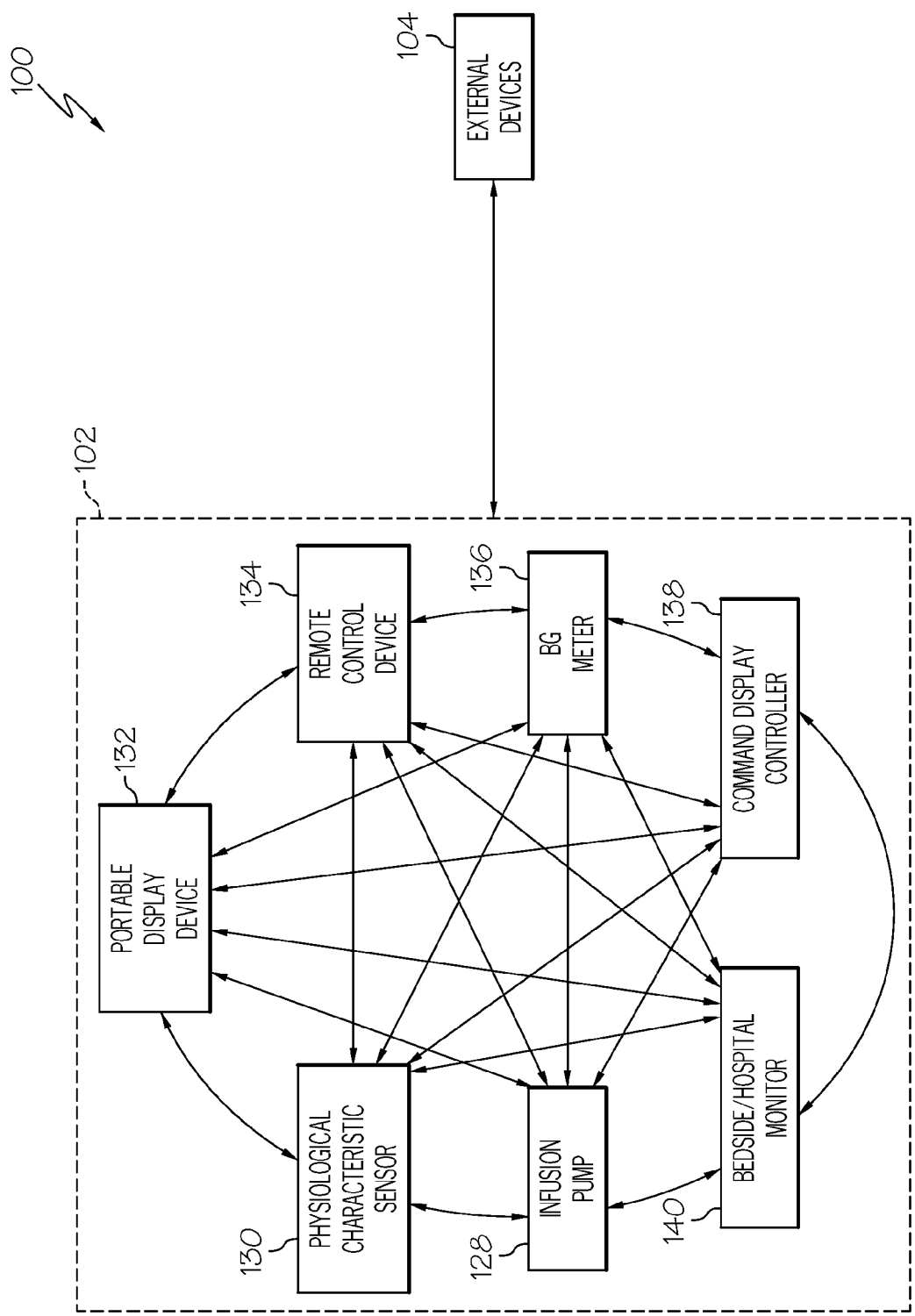
FIG. 1 is a schematic representation of a medical device system that includes wireless devices.

Although the disclosed subject matter relates generally to wireless devices regardless of their particular implementation or purpose, a medical device application is described here. FIG. 1 is a schematic representation of a medical device system 100 configured in accordance with an exemplary embodiment. In this example, the system 100 is an insulin infusion system that controls the infusion of insulin into the body of a user, although aspects of the system 100 may also be utilized in the context of other medical device systems. Briefly, the system 100 includes a local infusion system 102 having one or more local devices configured to wirelessly communicate with each other. This description may refer to the local infusion system 102 as a "personal area network" or a "body area network" of its constituent devices. Moreover, the local devices in the local infusion system 102 may be capable of communication (unidirectional or bidirectional) with one or more "external" devices 104 that are not considered to be part of the local infusion system 102. The manner in which a given local device within the local infusion system 102 communicates with a given external device 104 may vary depending upon the particular configuration of the system 100, the characteristics of the local device, and the characteristics of the external device 104. For example, data may be routed between the local infusion system 102 and an external device 104 using one data communication network, using a plurality of data communication networks, using a direct wireless or wired connection, or the like.

In an embodiment, local devices within the local infusion system 102 may be suitably configured to support the transmission of data to various external devices 104, such as, without limitation: a stationary monitor device, such as a bedside monitor or a piece of hospital monitoring equipment; a portable computer, such as a laptop PC, a palmtop PC, or a tablet PC; a stationary computer, such as a desktop PC; a personal digital assistant, which may also be a portable email device; a smart phone, which may also be a portable email device; a wireless phone, such as a cellular phone or a cordless phone; one or more additional computing devices or databases; or the like. The above list of possible external devices 104 is not exhaustive, and an implementation of the system 100 can be designed to accommodate communication with other systems, equipment, computing devices, components, and elements that are external to the local infusion system 102.

In one embodiment, the local infusion system 102 is realized as an insulin infusion system that is locally controlled and monitored by the patient. In this example, the local infusion system 102 includes at least an infusion pump 128. The local infusion system 102 may also include any of the following components, without limitation: a physiological characteristic sensor 130, such as a continuous glucose sensor (which may include a wireless transmitter); a portable display device 132; a remote control device 134; a BG meter 136 or other physiological characteristic meter; a command display controller 138 for the infusion pump 128; and a monitor 140, which may be realized as a bedside monitor or a hospital monitor.

As depicted in FIG. 1, these local devices may be configured to transmit and receive local communications within the local infusion system 102, where such local communications are transmitted and received in accordance with one or more specified local data communication protocols. For example, local communications may be exchanged between local devices using one or more wireless data communication protocols (which may leverage RF, infrared, magnetic induction, or other wireless techniques) and/or using one or more wired data communication protocols. Thus, one or more of the local devices can be considered to be a wireless medical device in the context of this description. The local infusion system 102 may be flexibly configured such that any given local device can communicate with any other local device, and a communication link or path between two local devices may be unidirectional or bidirectional. FIG. 1 depicts an exemplary embodiment where each communication link or path is bidirectional (represented by double headed arrows).

The infusion pump 128 is configured to deliver fluid, such as insulin, into the body of a user via, for example, an infusion set. In accordance with one exemplary embodiment, the infusion pump 128 initially (or by default) serves as a central hub or wireless coordinator, and much of the processing logic and intelligence for the local infusion system 102 resides at the infusion pump 128. In some embodiments, the local medical device system need not include the infusion pump 128, for example, monitoring systems utilized in conjunction with traditional insulin injection therapy. Moreover, the infusion pump 128 need not include a display. In an embodiment that lacks a display, the portable display device 132, the remote control device 134, the command display controller 138, or any other device within the local infusion system 102 may serve as a remote display for the infusion pump 128. Other options for a remote display include, but are not limited to, any of the external devices 104 described above, e.g., a wireless phone, a monitor device, a portable computer, or a personal digital assistant.

In practice, operation of the infusion pump 128 may be remotely controlled by the command display controller 138 (which may be realized as a handheld monitor/controller for the infusion pump 128), by the remote control device 134, and/or by or the monitor 140. In one exemplary embodiment, the BG meter 136 may include the functionality of a controller device such that both components share a single housing. Control of the infusion pump 128 may also be possible via a suitably configured user interface located at the infusion pump 128 itself.

The local infusion system 102 may also include the physiologic characteristic sensor 130, which is suitably configured to measure a physiologic characteristic of the patient. In addition, the sensor 130 may include processing and control logic that enables it to control the operation of the infusion pump 128. Such control may be responsive to measurements obtained by the sensor 130. In the exemplary system described here, the sensor 130 is a continuous BG sensor that measures the BG level of the patient in real time. The sensor 130 may include a wireless transmitter that facilitates transmission of physiologic data of the user to other devices within the local infusion system 102. Alternatively, the sensor 130 may be directly wired to a monitor/user interface. The sensor 130 may also be linked to the monitor 140 so that monitoring and programming of medication delivery may be performed remotely. Alternatively, the sensor 130 may communicate directly with devices in the external network space, e.g., via Bluetooth, ZigBee or the like.

Local devices can process the received sensor data in an appropriate manner. For example, the portable display device 132, the remote control device 134, the BG meter 136, the command display controller 138, the monitor 140, or the infusion pump 128 may display the current BG level derived from the received sensor data and/or generate an alert or otherwise indicate low or high BG levels. As another example, the BG meter 136 or the infusion pump 128 may process the received sensor data for purposes of calibration. As yet another example, the infusion pump 128 may be configured to activate its infusion mechanism in response to the received sensor data. Moreover, sensor data could be processed in one or more of the local devices and/or in one or more of the external devices 104. In this regard, the system 100 may utilize distributed processing techniques for the handling of sensor data.

Any of the devices within the local infusion system 102 may include a display and related processing logic that facilitates the display of physiologic patient data, device status information, time and date information, alarm/alert status, and other information related to the operation, status, or condition of the patient, related to any of the devices within the local infusion system 102, or related to the local infusion system 102 itself. The portable display device 132 may be realized as a small device having limited functionality. In this regard, the portable display device 132 may be incorporated into a key fob, a carabiner, a pendant, an insulin pen, a credit card display, or the like. Other local devices may have expanded display capabilities related to the specific functionality of such devices. For example, the BG meter 136 may include display features that are specific to its metering functionality.

The BG meter 136 is generally configured to measure the BG level of a user by analyzing a blood sample. For example, the BG meter 136 may include a receptacle for receiving a blood sample test strip. In this regard, the user inserts a test strip into the BG meter 136, which analyzes the sample and displays a BG level corresponding to the test strip sample. The BG meter 136 may be configured to generate a local communication, which conveys the measured BG level, for transmission to other local devices within the local infusion system 102. Depending upon the specific application, the BG meter 136 may also include the functionality of a monitoring device for the infusion pump 128 and/or the functionality of a controller device for the infusion pump 128.

The command display controller 138 is preferably realized as a handheld monitor/controller device that, although physically separate from the infusion pump 128, enables the user to monitor and control the operation of the infusion pump 128. This allows the user to operate the infusion pump 128 without physically handling the device. The command display controller 138 may include a communication module for transmitting local communications or commands to the infusion pump 128. In further embodiments, the command display controller 138 may receive local communications sent from the infusion pump 128 or other components within the local infusion system 102. In exemplary embodiments, the command display controller 138 also includes a network communication module for handling network communications to and from network devices that are external to the local infusion system 102. Further, the command display controller 138 may include one or more user input elements on its housing, such as keys, buttons, or the like, which accommodate user inputs. In certain embodiments, the command display controller 138 includes a display on its housing, which may be configured to concurrently reproduce at least a portion of the information displayed on the infusion pump 128.

The monitor 140, which may be realized as a bedside monitor for personal use or as a hospital monitor for caregiver use, enables remote monitoring of the infusion pump 128 (and possibly other devices within the local infusion system 102). The monitor 140 and other monitors described herein may be utilized in applications that do not utilize the infusion pump 128; for example, applications that monitor patient data (such as glucose levels). In addition, the monitor 140 may be suitably configured to enable remote programming and control of the infusion pump 128 and/or other devices within the local infusion system 102. In this regard, a "monitor" as used herein can generally refer to a monitor-only device or a monitor-controller device. In practice, the monitor 140 is a relatively large device in comparison to portable or handheld devices of the local infusion system 102. In contrast to the remote control device 134, the portable display device 132, and the command display controller 138, the monitor 140 is intended to be somewhat stationary and not carried by the user. For example, a bedside monitor may be located on a nightstand beside the patient's bed, while a hospital monitor may be located on a medical equipment cart or stand in the patient's room. In contrast to the smaller portable devices of the local infusion system 102, the monitor 140 preferably includes a large and easy to read display element, which may be configured to concurrently reproduce at least a portion of the information displayed on the infusion pump 128.

As described above in connection with the command display controller 138, the monitor 140 may also be configured to allow the user to remotely operate the infusion pump 128. The monitor 140 may include a communication module for receiving and/or transmitting local communications within the local infusion system 102. Moreover, the monitor 140 may include a network communication module for handling network communications to and from network devices that are external to the local infusion system 102. Further, the monitor 140 may include one or more user input elements on its housing, such as keys, buttons, or the like, which accommodate user inputs.

As shown in FIG. 1, the local infusion system 102 is capable of establishing many potential communication paths between the local devices. In certain embodiments, a controller device (e.g., the remote control device 134, the command display controller 138, or the monitor 140) may serve as a translator between the infusion pump 128 and the other components of the local infusion system 102, such as the BG meter 136. For example, the controller device may have the ability to determine how best to translate data received from the infusion pump 128 for compatibility with the display requirements of a destination device within the local infusion system 102. As depicted in FIG. 1, the infusion pump 128 may communicate directly with the BG meter 136. In some embodiments, the local infusion system 102 may include multiple controllers that can communicate with the infusion pump 128. In other embodiments, only one controller device can communicate with the infusion pump 128 at any given moment. The controller device functionality may also be integrated into the infusion pump 128 in some embodiments. In yet another embodiment, the BG meter 136 may be integrated into the controller device such that both features share a single device housing.

At least two devices in the local infusion system 102 are preferably capable of supporting wireless data communication with each other. The embodiments described herein employ wireless beacons (transmitted by at least one beacon-transmitting device, typically designated as the coordinator device in a wireless network of devices) for purposes of wireless communication management. A beacon is a transmission from a device in a wireless network to which other devices are synchronized. For example, beacons are transmitted periodically from the coordinator (the hub) of a star network. Different end node devices within the network know the beacon transmission period and "listen" for beacons in accordance with the designated period (or multiples thereof) to synchronize their timing, listen for messages, and/or respond with messages.

Figure 2:
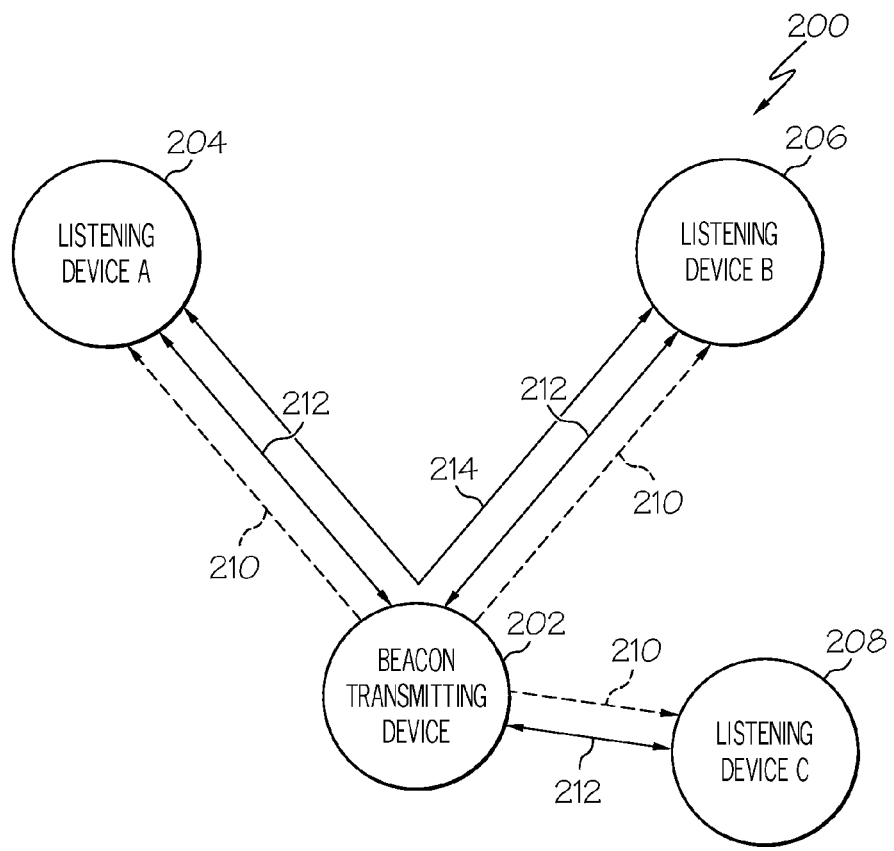
FIG. 2 is a diagram that depicts four wireless devices arranged in a star network configuration.

A plurality of wireless devices in the local infusion system 102 can be arranged and configured to operate in any suitable network topology. For example, the wireless devices may be arranged in a star network topology, a mesh network configuration, a tree network topology, an ad-hoc network topology, or the like. In this regard, FIG. 2 is a diagram that depicts four wireless devices arranged in a star network configuration 200 having a beacon-transmitting wireless device 202 and three listening wireless devices 204, 206, 208. This exemplary star network configuration 200 is shown here for ease of description, and is not intended to limit or otherwise restrict the scope of the disclosed subject matter.

In the star network configuration 200, the designated beacon-transmitting wireless device 202 may be referred to as the "hub" or "coordinator" device, where the beacon-transmitting wireless device 202 generates and transmits wireless beacons 210, which can be received by the designated listening wireless devices 204, 206, 208. For this implementation, listening wireless devices 204, 206, 208 do not generate or transmit wireless beacons. Moreover, the beacon-transmitting wireless device 202 can directly communicate with any of the listening wireless devices 204, 206, 208 (as represented by the solid arrows 212 in FIG. 2). When functioning as the hub or coordinator device, the beacon-transmitting wireless device 202 facilitates communication between the listening wireless devices 204, 206, 208 by acting as a wireless repeater, router, or redirector with or without modifications to facilitate such communication. For example, the solid arrow 214 in FIG. 2 schematically illustrates the manner in which the beacon-transmitting wireless device 202 can wirelessly route data between the listening wireless device 204 and the listening wireless device 206. Notably, for this implementation the listening wireless devices 204, 206, 208 are unable to directly communicate with each other in the star network configuration 200. Rather, the beacon-transmitting wireless device 202 must be utilized as the wireless router between the listening wireless devices 204, 206, 208.

Figure 3:
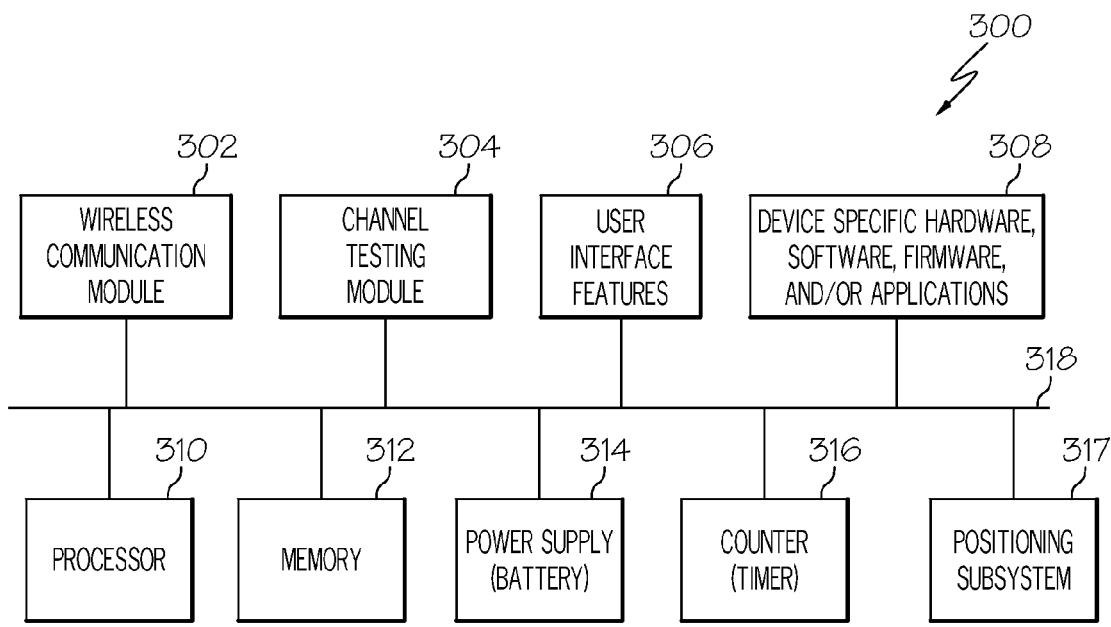
FIG. 3 is a schematic representation of an exemplary embodiment of a wireless device.

FIG. 3 is a schematic representation of an exemplary embodiment of a wireless device 300 suitable for use with certain wireless channel hopping, channel adaptation, and other techniques and protocols described here. The wireless device 300 may be suitably configured to support the particular application and system architecture. For example, the wireless device 300 may represent, without limitation: a wireless medical device, such as one of the devices in the local infusion system 102 (FIG. 1); a wireless computing device; a mobile communication device; or the like. FIG. 3 depicts a generalized configuration that could be used for a coordinator device, an end node device, or a device that can perform both roles (i.e., function as either a coordinator or an end node device as necessary).

For the illustrated embodiment, the wireless device 300 includes: a wireless communication module 302; a channel testing module 304; one or more user interface (UI) features 306; device specific hardware, software, firmware, and/or applications 308; a processor 310; a suitable amount of memory 312; a power supply 314, such as a rechargeable or replaceable battery; a counter/timer 316; and a positioning subsystem 317. An implementation of the wireless device 300 may include additional functional elements and components that are suitably configured to support traditional or well known features, which will not be described in detail here. The elements of the wireless device 300 may be coupled together via a bus 318 or any suitable interconnection architecture.

The processor 310 may be implemented or performed with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. The processor 310 may be realized as a microprocessor, a controller, a microcontroller, or a state machine. Moreover, the processor 310 may be implemented as a combination of computing devices, e.g., a combination of a digital signal processor and a microprocessor, a plurality of microprocessors, one or more microprocessors in conjunction with a digital signal processor core, or any other such configuration.

The memory 312 may be realized as RAM memory, flash memory, EPROM memory, EEPROM memory, registers, a hard disk, a removable disk, a CD-ROM, or any other form of storage medium known in the art. In this regard, the memory 312 can be coupled to the processor 310 to enable the processor 310 to read information from, and write information to, the memory 312. In the alternative, the memory 312 may be integral to the processor 310. As an example, the processor 310 and the memory 312 may reside in an ASIC. As explained in more detail below, the memory 312 may be employed to save and maintain data and information that is used in connection with certain wireless channel hopping and adaptation techniques. For example, the memory 312 could be used to save ping timing information and/or ping schedules received from end node devices. As another example, the memory 312 could be used to save and maintain an ordered list of wireless channels available to a coordinator device. In certain embodiments, the memory 312 is utilized to maintain and update a location-correlated channel list that includes entries that correlate designated local areas to preferred wireless channels that work well in or near those designated local areas.

The device-specific hardware, software, firmware, and/or applications 308 may vary from one embodiment of the wireless device 300 to another. For example, a wireless infusion pump device can be implemented in different formats to address the needs of the particular application. On the other hand, a wireless controller device will have a different feature set and different operating capabilities. Accordingly, the device-specific hardware, software, firmware, and/or applications 308 will support the functions, operations, and processing requirements of the particular implementation of the wireless device 300. In practice, certain portions or aspects of the device-specific hardware, software, firmware, and/or applications 308 may be implemented in one or more of the other blocks depicted in FIG. 3.

The wireless device 300 employs at least one wireless communication module 302. In certain embodiments, the wireless device 300 also employs at least one wired/cabled communication module (not shown). These communication modules are suitably configured to support wireless/wired data communication (unidirectional or bidirectional, depending upon the particular implementation) between the wireless device 300 and other devices in the system.

The wireless communication module 302 is configured to support one or more wireless data communication protocols. Any number of suitable wireless data communication protocols, techniques, or methodologies may be supported by the wireless device 300, including, without limitation: RF; IrDA (infrared); BLUETOOTH®; ZigBee (and other variants of the IEEE 802.15.4 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. In certain deployments, the wireless communication module 302 implements a wireless protocol that is based upon the IEEE 802.15.4 protocol, with some modifications, additions, and/or changes. In an embodiment of the wireless device 300, a wireless data communication module may include or be realized as hardware, software, and/or firmware, such as an RF front end, a suitably configured radio module (which may be a stand alone module or integrated with other or all functions of the device), a wireless transmitter, a wireless receiver, a wireless transceiver, an infrared sensor, an infrared diode and sensor, an electromagnetic transducer, or the like. Moreover, the wireless device 300 may include one or more antenna arrangements that cooperate with the wireless data communication module.

As described in more detail below, the wireless communication module 302 may be suitably configured and controlled to transmit wireless beacons (if the wireless device 300 is designated as a beacon-transmitting coordinator device) or suitably configured and controlled to receive wireless beacons (if the wireless device 300 is designated as an end node device). The wireless communication module 302 is also configured to transmit and receive wireless packets of data while performing wireless data communication with other wireless devices. In particular embodiments, the wireless communication module 302 is suitably configured to support wireless data communication using designated or "preferred" wireless channels that are included in a location-correlated list of wireless channels for the wireless device 300.

The wireless device 300 may also be designed to accommodate UI features 306 that allow the user to control the operation of wireless device 300 and/or other devices within the system. The UI features 306 may include a keypad, keys, buttons, switches, knobs, a touchpad, a joystick, a pointing device, a virtual writing tablet, a display element, a speaker or other audio transducer, indicator lights, or any device, component, or function that enables the user to select options, input information, obtain audio information, obtain visual information, or otherwise interact with the wireless device 300 and/or other devices within the system.

The counter/timer 316 may be utilized in some embodiments of wireless device 300 to count or otherwise monitor for missed ping packets or messages, which the wireless device 300 (when operating as a coordinator device) normally expects to receive from end node devices. As described in more detail below, the counter/timer 316 may be designed to count the number of successive or sequential missed ping messages, as an indicator of wireless channel quality and/or wireless synchronization.

The channel testing module 304 performs certain diagnostic tests as needed during the operation of the wireless device 300. For example, the channel testing module 304 can be used to test the quality of the wireless channel(s) currently being used by the wireless device 300. The channel testing module 304 could also be used to test the quality of other available wireless channels, for purposes of quality ranking and possible selection as a secondary wireless channel. These diagnostic procedures are described in more detail below.

The positioning subsystem 317 is suitably configured to determine, calculate, and/or obtain location data that is indicative of the current geographic position of the wireless device 300. This location data can be used in the manner described below for purposes of location-correlated assignment and selection of wireless channels. In certain implementations, the positioning subsystem 317 includes or cooperates with a global positioning system (GPS) receiver. In preferred embodiments, the GPS receiver is integrated into the wireless device 300, and the GPS receiver can be located within the chassis or housing of the wireless device 300. In alternative implementations, the positioning subsystem 317 could be suitably configured to support other positioning and/or location-based techniques, services, or technologies. For example, the positioning subsystem 317 may be configured to support wireless triangulation techniques, which could be provided in connection with cellular telephone providers, wireless local area network infrastructure equipment, or the like.

In operation, the wireless device 300 may be a beacon-transmitting coordinator device or a listening end node wireless device, depending upon the particular application, the system configuration, the network topology of the wireless devices in the system, the current operating status of the wireless devices in the system, and/or other factors. For example, in FIG. 2, the star network configuration 200 includes only one beacon-transmitting wireless device 202, and the remaining wireless devices are designated as listening wireless devices 204, 206, 208. Nonetheless, each wireless device depicted in FIG. 2 may be generally implemented as depicted in FIG. 3.

Wireless medical devices in a body area network may be suitably configured to support one or more of the enhanced wireless features described here. Briefly, these enhancements generally relate to the following features: (1) wireless coordinator switching; (2) variable beacon intervals; (3) wireless channel hopping; (4) channel interference adaptation; and (5) location-correlated wireless channel management.

Wireless Coordinator Switching

The embodiment of the body area network of wireless medical devices described here designates one (and only one) device as the wireless coordinator device at any given time, and designates all other devices as wireless end node devices. The coordinator device may also be referred to as the network hub or the beacon-transmitting device (see FIG. 2). Although only one coordinator device is designated at any given time, the body area network accommodates the dynamic switching of device roles such that a particular device may function as the coordinator device or as an end node device, depending upon the specific operating conditions, user preferences, network status, and/or other considerations. Indeed, each device in the body area network could be deployed and suitably configured with both coordinator and end node functionality.

In practice, the currently designated coordinator device and/or any end node device (alone or in cooperation with one another) will be responsible for determining conditions, operating states, or status that indicates a "mode switching" event. In response to the detection of such a mode switching event, the body area network will be reconfigured such that a new coordinator device is designated. In addition, the previously designated coordinator device will begin operating as an end node device. A given wireless device in a body area network need not support this coordinator switching feature. In other words, some of the wireless devices may operate in a "fixed" manner as end node devices.

While functioning as the designated coordinator device in the personal area network, a wireless device transmits beacons (intended for receipt by end node devices), but it does not receive beacons from end node devices. While functioning as an end node device, however, a wireless device receives beacons (from the designated coordinator device), but it does not send beacons. Accordingly, a "coordinator switchable" wireless medical device is suitably configured with appropriate hardware, software, processing logic, and functionality to transmit beacons (while functioning as the designated coordinator device) and to receive beacons (while functioning as an end node device). In practice, coordinator switchable devices may wirelessly communicate with one another in an appropriate manner and using particular messages, packets, or data that represents commands or instructions that prompt the switching of modes (i.e., switching from coordinator to end node, or switching from end node to coordinator).

A body area network of wireless medical devices could implement certain protocols and features that facilitate communication between its wireless devices for purposes of coordinator switching. For example, access to an exemplary embodiment of a body area network of medical devices is controlled using a vendor/manufacturer identifier that is included in the unique address of each device in the network. In certain implementations, the vendor/manufacturer identifier is a three-byte field that is typically found at the beginning of the eight-byte device address (the device address may be globally unique, it may be unique within the network, or it may be unique within a specified geographic or other defined area or region). This allows a manufacturer of individual components to control whether or not a body area network can be established. Thus, if an infusion pump device, a controller device, and a physiological sensor transmitter device are all manufactured, sold, or offered together as a set or are otherwise intended to be compatible with one another, then a common vendor/manufacturer identifier can be issued to all of those devices. Moreover, this allows any wireless device with a specified vendor/manufacturer identifier (e.g., an identifier associated with a particular company such as Medtronic, Inc.) to operate as the coordinator device for other wireless devices having the same vendor/manufacturer identifier. Thus, a network deployment that includes wireless devices from two different manufacturers or vendors may have some coordinator switchable devices (e.g., those provided and supported by one company) and other devices that are incompatible with the coordinator switching feature (e.g., those provided and supported by a different company).

In particular embodiments, device addresses are used to control access to the body area network of medical devices—a device will be allowed access to the network only if it has an allowable or authorized device address. Thus, in order for two devices to communicate with each other in such a network, at least one of the two devices must be aware of the device address of the other device. In this regard, a given wireless device can be programmed with the device addresses of other wireless devices in any appropriate manner (e.g., user-entered data, pre-configuration or pre-programming at the factory, exchange of device addresses during an initial scanning procedure, or the like). Various techniques, methodologies, and applications related to device identifiers are described in United States Patent Application Publication number US 2007/0253021 A1, the relevant content of which is incorporated by reference herein.

Use Case Example: Out of the Box Operation

A body area network may include a plurality of wireless medical devices that are initially deployed together "out of the box" so to speak. In such a scenario, a given wireless device may not know whether it should initially be the designated coordinator device or an end node device. For example, a body area network may include a glucose sensor transmitter that has no user interface, and an insulin pump. Under normal circumstances, the glucose sensor transmitter will be an end node if the insulin pump (which will be the coordinator by default) is within wireless range. That said, there are some situations where the glucose sensor transmitter may need to function as the coordinator device. Consequently, when first deployed (or after any re-initialization event), the glucose sensor transmitter will automatically switch between coordinator and end node modes. In this regard, the glucose sensor transmitter will listen for beacons while functioning as an end node device for a period of time, switch modes, and then transmit beacons while functioning as the coordinator device for another period of time. For this example, only the glucose sensor transmitter device will carry out this automatic mode switching out of the box, due to its lack of a user interface.

If the body area network includes a wireless controller device (that remotely controls another wireless device such as an insulin pump), then the controller device in certain embodiments will by default be designated as the coordinator device. This default configuration ensures that the controller device initially functions as the coordinator device out of the box and immediately after any re-initialization event. Moreover, the slave device (or devices) that are controlled by the controller device will function as end node devices by default. Accordingly, if an insulin pump, a glucose sensor transmitter, and a controller device are initially deployed together, then the controller device will automatically begin operating as the coordinator device, and the insulin pump will automatically begin operating as an end node device. As described above, the glucose sensor transmitter will change its role (as a coordinator and an end node) until it determines that the controller device is the designated coordinator device. Thereafter, the glucose sensor transmitter will configure itself to function as an end node device.

In another embodiment where the glucose sensor transmitter has no user interface (and, therefore, its operation will be completely automated), the glucose sensor transmitter would normally be designated as the network coordinator device because it may need to communicate with a controller device, a portable monitor device, a patient-worn infusion device, or the like. In such cases, the glucose sensor transmitter could start beaconing (as the coordinator device) for a designated period of time, such as thirty seconds, to enable a controller device or other devices to associate with it. If such an association occurs, then the glucose sensor transmitter will remain the network coordinator. If, however, nothing happens during the thirty second window, the glucose sensor transmitter could search for other network coordinators (acting as an end node device) for a period of time. If during this period of time the glucose sensor transmitter finds a coordinator device and successfully associates with it, then the glucose sensor transmitter will function as an end node device. In practice, the glucose sensor transmitter could alternate this routine for as long as its battery permits.

Use Case Example: Temporary Disabling of Wireless Transmissions

In certain situations it may be necessary to temporarily disable wireless transmissions from devices in a personal area network. For example, during takeoff and landing of an aircraft, wireless devices must be disabled or powered off to reduce the amount of electromagnetic interference onboard the aircraft. Thus, wireless devices in a body area network should support temporary disabling of wireless transmissions (including wireless beacons). Wireless transmission at the coordinator device could be disabled using, for example, a remote controller device or some other end node device that has a suitable user interface. If, however, the designated coordinator device lacks a user interface, then it may be challenging or impossible to reactivate its wireless transmission capability.

The coordinator switching feature can be implemented in a way that addresses the scenario described above. In this example, before entering the "airplane mode" and disabling wireless transmissions, an end node device with a user interface (such as a controller device) and the currently designated coordinator device (which has no user interface) will switch coordinator roles. Thereafter, the devices can enter the airplane mode to temporarily disable wireless transmissions. At this time, the device with a user interface is the designated coordinator device. Thus, the user interface of the temporary coordinator device can be manipulated as needed to exit the airplane mode. This activates the wireless transmission capability of the temporary coordinator device, which allows the temporary coordinator device to resume sending beacons to the end node devices (in the airplane mode, end node devices can still receive beacons). After exiting the airplane mode, the temporary coordinator device can send a beacon or other "activate" message to the end node devices. Thereafter, the temporary coordinator device and the normally designated coordinator device can switch back to their usual roles.

Variable Beacon Intervals

According to the IEEE Specification 802.15.4, devices in a wireless personal area network are synchronized to one another by way of network beacons, which are transmitted by the coordinator device at a fixed interval. Thus, all end node devices expect to receive beacons on the same schedule and at synchronized time slots. In contrast, a body area network of wireless medical devices as described here can be suitably configured to use variable or flexible beacon intervals, depending upon certain operating conditions. For example, the end node devices can be designed to listen for each and every beacon, every other beacon, every third beacon, or the like. This enables each individual end node device to determine or select how often it needs to "wake up" to receive a beacon, with the assumption that the coordinator device transmits beacons at a known and fixed interval. Accordingly, the end node beacon interval will be some multiple of the fixed interval used by the coordinator device. For instance, if the coordinator device sends beacons at one-second intervals, an end node device will be configured to listen for beacons at one-second intervals, two-second intervals, three-second intervals, and so on.

In certain embodiments, the particular beacon interval used by a given end node device will be dictated or influenced by its desired battery life, the battery capacity, typical use patterns, the desired wireless communication availability, etc. The interval for a given device could be preconfigured, programmed, and fixed, or it may be variable, user-configurable, or dynamically adjustable. For example, out of the box a glucose sensor transmitter might initially listen for beacons more frequently (e.g., every two seconds), but switch to a longer interval after it establishes contact with the coordinator device. In practice, this technique can save power (e.g., battery life) at the end node devices, since the end node devices need not listen for beacons at an unnecessarily high rate.

Various techniques, methodologies, and applications related to device identifiers are described in U.S. patent application Ser. No. 12/265,673, which corresponds to U.S. Patent Publication number US 2010/0111066. The relevant content of this patent application is incorporated by reference herein.

Wireless Channel Hopping

Certain embodiments of a body area network of wireless devices are suitably configured to switch wireless channels as needed to address poor wireless performance, channel quality degradation, and the like. This feature is particularly suitable for wireless medical device networks, where robust and continuous wireless connectivity between devices is desirable, and where the body area network is portable (with the patient) and, therefore, susceptible to different operating environments. In this regard, each compatible end node device in the network will report to the coordinator device its ping interval, schedule, or timing information, which indicates when that end node device will transmit a wireless ping to the coordinator device. A wireless ping could represent a dummy packet that is sent if the end node device has no "real" data to send to the coordinator device. Pings (in the context of this description) could represent a scheduled or periodic transmission of which both the end node device and the coordinator device are aware. For example, the glucose sensor transmitter could transmit a glucose data packet once every minute, and the glucose sensor transmitter and infusion pump are both aware of this expected one-minute transmission, so these glucose data packets could be used instead of using devoted ping/dummy packets. Thus, pings sent by an end node device are similar to beacons sent by the coordinator device, because they are sent at specified times and, therefore, pings can be expected at the coordinator device. For this example, the coordinator device maintains a table or database of the respective ping schedules for the different end node devices. If the coordinator device determines that it has missed a number of pings from an end node device, then the coordinator device enters a diagnostic mode to test the current wireless channel. If the coordinator device determines that the current wireless channel is noisy or is otherwise of poor quality, then it can take appropriate action to switch to a different wireless channel.

Figure 4A:
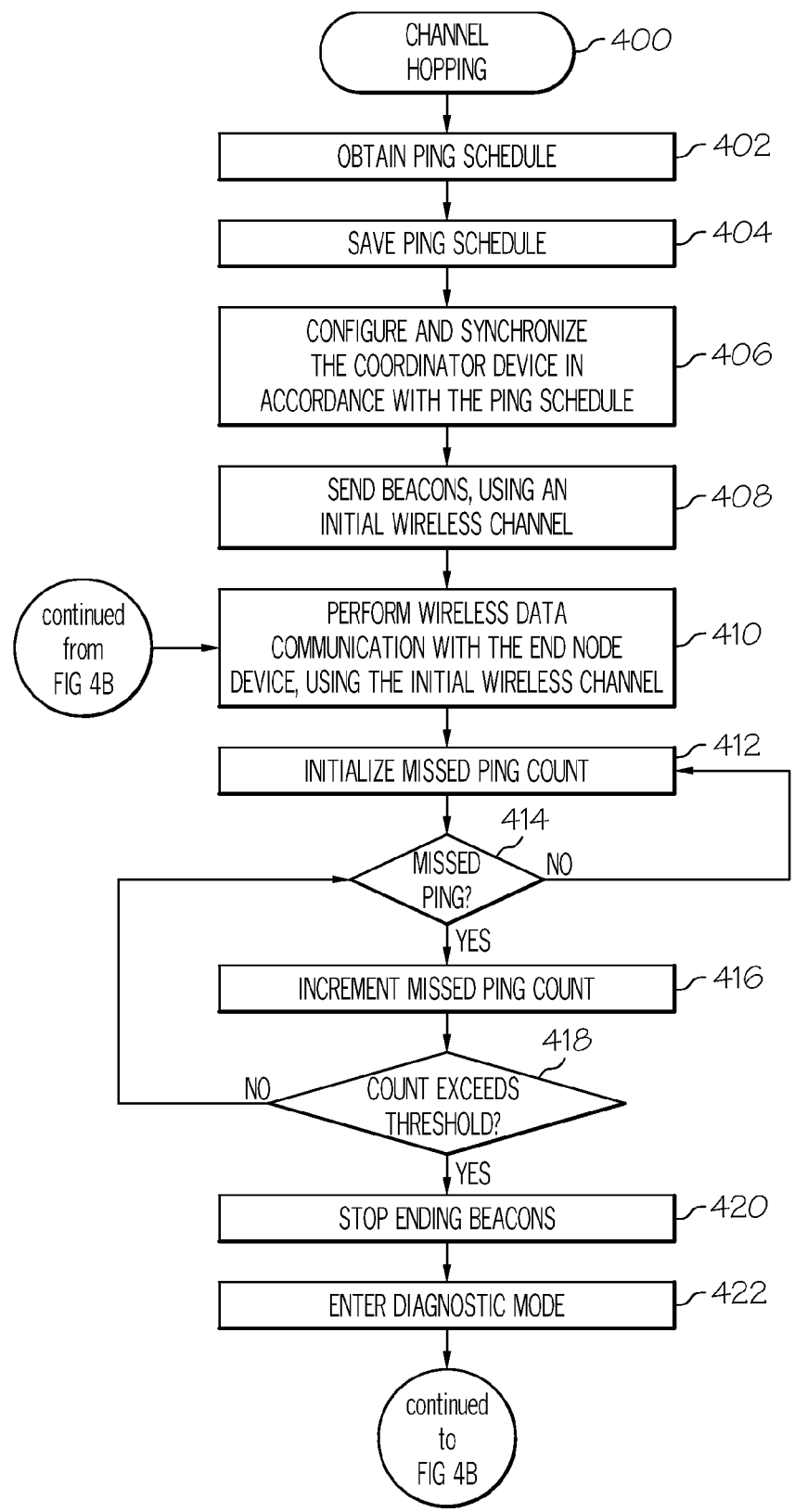
FIG. 4 is a flow chart that illustrates an exemplary embodiment of a channel hopping process.
Figure 4B:
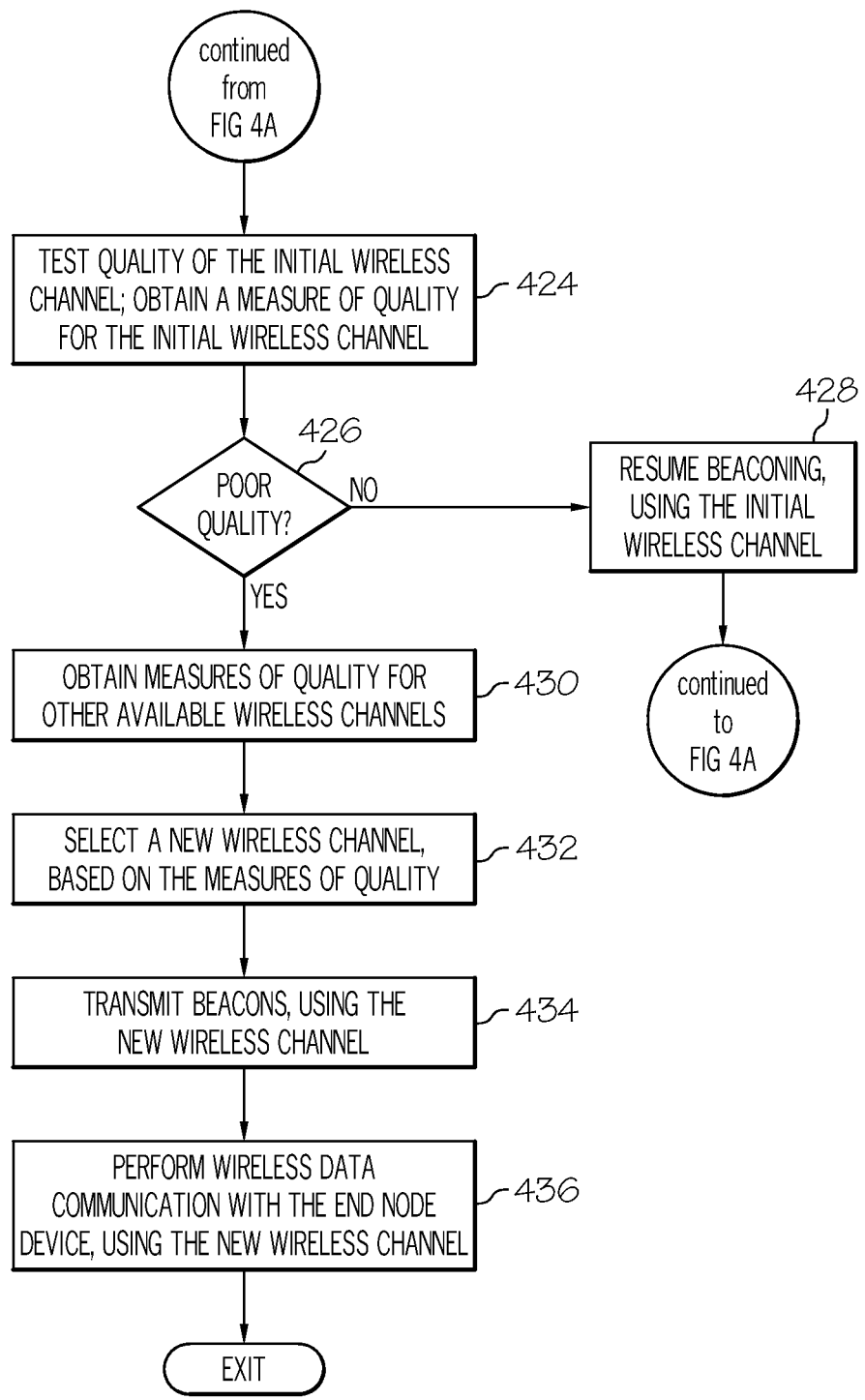

FIG. 4 is a flow chart that illustrates an exemplary embodiment of a channel hopping process 400, which may be performed by a coordinator device in a wireless network. The various tasks performed in connection with process 400 may be performed by software, hardware, firmware, or any combination thereof. For illustrative purposes, the following description of process 400 may refer to elements mentioned above in connection with FIGS. 1-3. It should be appreciated that process 400 may include any number of additional or alternative tasks, the tasks shown in FIG. 4 need not be performed in the illustrated order, and process 400 may be incorporated into a more comprehensive procedure or process having additional functionality not described in detail herein. Moreover, one or more of the tasks depicted in FIG. 4 could be omitted if the intended functionality is preserved.

This embodiment of the process 400 may begin by obtaining, at the wireless coordinator device, a ping schedule for a wireless end node device (task 402). This description considers a basic scenario where the network includes a coordinator device and only one end node device. In practice, the coordinator device and process 400 can support any number of different end node devices and the tasks described here can be modified or extended to support a plurality of end node devices. The ping schedule could be obtained by programming the coordinator device at the factory, by the user during an initialization procedure, by a physician or caretaker before the system is deployed, or the like. In some embodiments, the coordinator device receives the ping schedule (wirelessly or otherwise) from the wireless end node device. The ping schedule includes, identifies, or otherwise indicates ping timing information corresponding to the end node device. This ping timing information might indicate time slots during which the coordinator device should expect to receive pings from the end node device, or it might designate a ping interval to be used by the end node device. Thus, when the coordinator device is synchronized with the end node device, the coordinator device will know in advance when to expect a ping from the end node device.

The ping schedule is saved at the wireless coordinator device (task 404) and is used to configure and synchronize the coordinator device for receipt of wireless pings from the end node device (task 406). Referring to FIG. 3, the ping schedule could be stored in the memory 312, for example. Thus, the coordinator device is adjusted, initialized, or otherwise set to receive pings from the wireless end node device in accordance with the saved ping schedule. This prepares the coordinator device to monitor for pings sent by the end node device according to its ping schedule. As mentioned above, the coordinator device could receive any number of ping schedules for any number of different end node devices, save those ping schedules, and configure itself in an appropriate manner to monitor for pings sent by the different end node devices in accordance with their respective ping schedules.

During operation, the coordinator device sends wireless beacons using an initial wireless data communication channel (task 408), and performs wireless data communication with the end node device using the initial wireless channel (task 410). Under normal or typical operating conditions, the coordinator device will also receive ping messages from the end node device, using the initial wireless channel. In certain embodiments, the system can potentially use any channel selected from a designated group of wireless data communication channels that have been allocated for use. For example, there may be a finite number of predefined wireless channels available for use within a specified frequency band, and the initial wireless channel (and other wireless channels used during process 400) will be one of those predefined channels. In practice, it may be desirable to specify a limited subset of available channels for the coordinator device to simplify processing overhead and/or to contemplate typical operating conditions and environments for the system.

Although not required of all embodiments, this example assumes that the coordinator device keeps track of missed pings (that are normally expected from the end node device), which could be an indication of poor wireless channel quality. In this regard, the coordinator device could detect loss of wireless synchronization with the end node device, based upon missed pings. For example, if the coordinator device detects that it has missed at least a threshold number of expected pings (as indicated by the ping schedule), then it might conclude that it has lost wireless synchronization with the end node device. Accordingly, the coordinator device may utilize or maintain a counter (such as the counter/timer 316 depicted in FIG. 3) for missed pings, and process 400 may initialize a missed ping count (task 412) for the initial wireless channel. Although not required, this description assumes that the missed ping count is initialized to a count of zero.

If the coordinator device fails to receive an expected ping (query task 414), then process 400 increments the missed ping count (task 416) by some amount. For this simple example, task 416 increments the missed ping count by one. If the currently held missed ping count exceeds a threshold count value (query task 418), then the coordinator device will cease the sending of wireless beacons on the initial wireless channel (task 420) and enter a diagnostic or test mode (task 422). The threshold count value used during query task 418 is chosen such that it accurately reflects conditions that can be attributed to loss of wireless synchronization. If the threshold count value has not been exceeded, then process 400 may return to query task 414 to monitor for more missed pings. This example relates to an implementation where the coordinator device considers consecutive or sequential missed pings (although an embodiment could alternatively monitor for missed pings that occur during a specified time period, whether or not they are consecutive). Therefore, if process 400 subsequently determines that an expected ping has not been missed (the "no" branch of query task 414), then the missed ping count is initialized again.

In response to detecting loss of wireless synchronization, the coordinator device enters the diagnostic mode (task 422) in an attempt to determine the cause of the missed pings. For this embodiment, the coordinator device tests the quality of the initial wireless channel and obtains a measure of quality for the initial wireless channel (task 424). Task 424 may test one or more quality characteristics, metrics, parameters, or quantities associated with the initial wireless channel. For example, the coordinator device can remain "tuned" to the initial wireless channel and measure the received signal strength, power, or energy caused by environmental noise and/or interference generated by nearby equipment. In certain embodiments, the coordinator device measures the noise on the initial wireless channel and the noise on at least one neighboring wireless channel because energy on channels at or near the frequency of the initial wireless channel could also impact the quality of wireless communication on the initial wireless channel itself.

If the obtained measure of quality fails to satisfy a threshold criteria or some stated quality metric, or is otherwise deemed to be indicative of poor channel quality (query task 426), then the coordinator device can proceed to a task 430. If, however, the quality of the initial wireless channel is above the threshold quality measure, then the coordinator device can resume beaconing using the initial wireless channel (task 428). Proceeding to task 428 in this manner is an indication that noise/interference on the initial wireless channel is tolerable and, therefore, the coordinator device assumes that the loss of synchronization is not due to poor channel quality. Rather, loss of wireless synchronization may have been caused by temporary disabling of the respective end node device. As another example, the coordinator device may lose synchronization with the end node device if for some reason the end node device is no longer within wireless range of the coordinator device (the user may have left the end node device at home while carrying the coordinator device to work). Under such scenarios, the coordinator device need not attempt to establish wireless connectivity on a different wireless channel, because doing so would be unnecessary and a waste of resources. As depicted in FIG. 4, after resuming beaconing with the initial wireless channel (task 428), the process 400 could be re-entered at an appropriate point, such as task 410.

Referring again to query task 426, if the coordinator device determines that the initial wireless channel is of poor quality, then the process may continue by obtaining measures of quality for at least one other available wireless channel (task 430). In practice, the wireless system will be capable of wireless communication using at least three different wireless channels. Accordingly, task 430 obtains, for a plurality of available wireless channels, a respective measure of wireless channel quality. In this regard, the coordinator device measures received signal strength, power, energy, or any measurable quantity on each of the other available wireless channels. After performing this channel scan, the coordinator device can select a new wireless channel for data communication with the end node device (task 432). Notably, this new wireless channel is selected from the set of available channels, and the selection is based upon the obtained measures of quality. In certain embodiments, the measure of wireless quality for the new wireless channel indicates the highest quality among the plurality of available channels. In other words, task 432 selects the "best" available wireless channel, as indicated by the obtained measures of quality. Alternatively, the coordinator device need not test the quality of all available channels before selecting the new wireless channel. Rather, the coordinator device could stop testing when it finds a good alternate channel. Thereafter, the coordinator device could designate that good channel as the new wireless channel without testing any more available channels.

After selecting the new wireless channel, the coordinator device switches to that new wireless channel and begins transmitting beacons to the end node device, using the new wireless channel (task 434). The end node device will eventually recognize that beacons are no longer being received on the initial wireless channel. In response to this condition, the end node device will perform a channel scan to listen for beacons on the different available wireless channels. Under normal operating conditions, the end node device will eventually receive the beacons sent by the coordinator device on the new wireless channel. Thereafter, the coordinator and end node devices will regain synchronization and the coordinator device can perform wireless data communication with the end node device using the new wireless channel (task 436). Although FIG. 4 depicts the process 400 ending at this point, it may be re-entered at task 412 to continue monitoring the quality of the new wireless channel in the manner described in detail above.

Channel Interference Adaptation

As explained in the preceding section, an exemplary embodiment of a body area network of medical devices can support an intelligent and dynamic channel hopping scheme that is influenced by wireless channel quality measurements. Certain embodiments of a body area network of wireless devices may also be configured to support user-specific interference adaptation techniques that prefer some wireless channels over other wireless channels. The general approach here is to weight the usability of the available wireless channels in a manner that is tailored to the user of the system. Assume, for this example, that five channels (A, B, C, D, and E) have been allocated for use with the body area network of medical devices. Initially (out of the box), the five channels may be listed in any order; for this example assume that the initial order is A, B, C, D, E. During an initialization period, the channels are tested in order until one satisfies a threshold quality measure. Any channel that fails the quality test during this time is placed at the bottom of the list to indicate its relatively lower preference, ranking, and/or priority. Accordingly, if channel A fails but channel B passes the quality test, then the rearranged channel order will be as follows: B, C, D, E, A. After the body area network is established, this channel order will be communicated to all of the end node devices.

During operation of the body area network of medical devices, the particular user might encounter different levels of wireless noise and interference. For example, channel B might be the best channel to use when the user is at home, but channel B may be noisy when the user is at the office. As another example, if the user goes to a neighbor's house and the currently designated wireless channel B is noisy, then the wireless coordinator device might detect loss of synchronization with end node devices and then switch to the next wireless channel in the list (channel C). In response to the network interruption, the coordinator device can test the available wireless channels and rearrange the order of the channels in the list in a manner that is weighted in accordance with the test results. The updated channel list can then be sent to the end node devices as before. This dynamic adaptation scheme can be designed such that channels that are of generally poor quality in many different locations gravitate towards the bottom of the list and, therefore, become less preferred and less frequently selected. In contrast, channels that are of generally high quality in commonly visited locations gravitate towards the top of the list and, therefore, become more preferred and more frequently selected. This routine enables the body area network to intelligently tune itself for better and more consistent wireless performance based upon the actual conditions and operating environments to which it is exposed.

Figure 5:
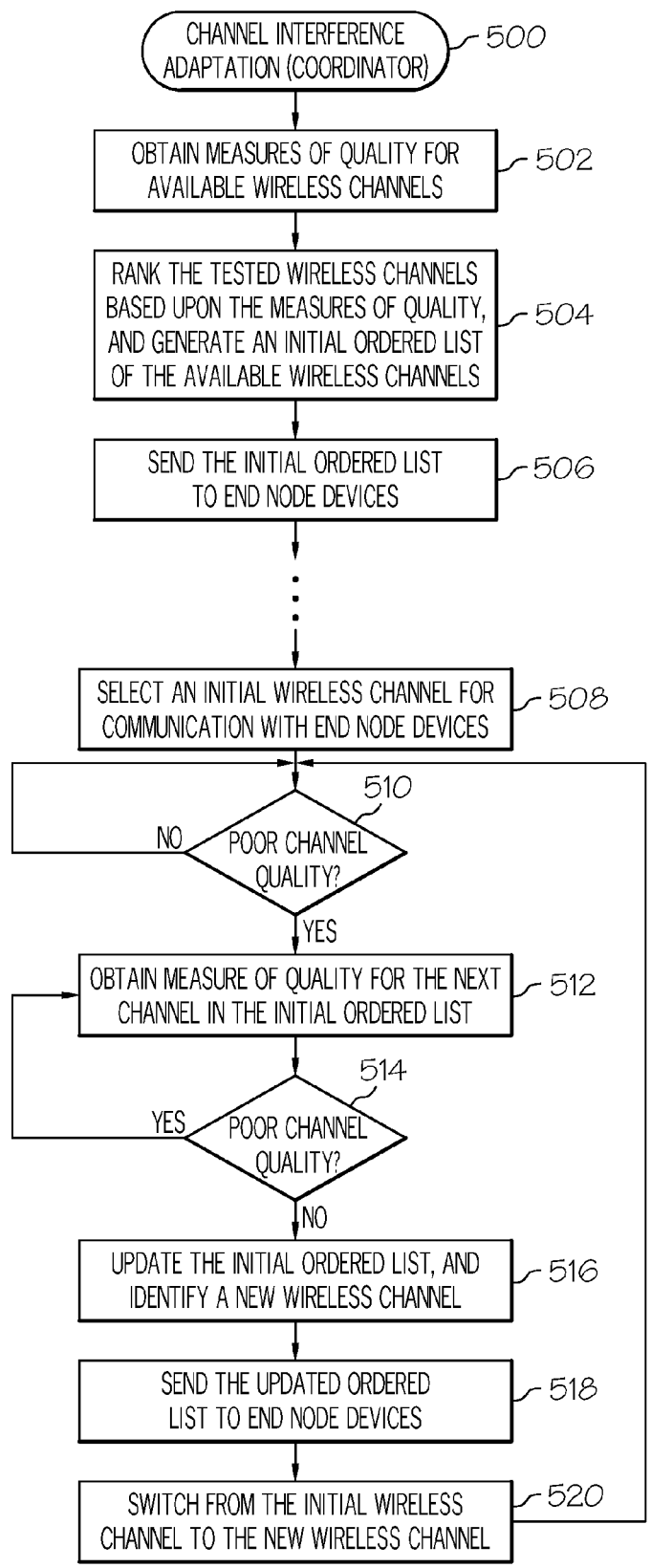
FIG. 5 is a flow chart that illustrates an exemplary embodiment of a channel interference adaptation process, which may be performed by a wireless coordinator device.

FIG. 5 is a flow chart that illustrates an exemplary embodiment of a channel interference adaptation process 500, which may be performed by a wireless coordinator device. The various tasks performed in connection with process 500 may be performed by software, hardware, firmware, or any combination thereof. For illustrative purposes, the following description of process 500 may refer to elements mentioned above in connection with FIGS. 1-3. It should be appreciated that process 500 may include any number of additional or alternative tasks, the tasks shown in FIG. 5 need not be performed in the illustrated order, and process 500 may be incorporated into a more comprehensive procedure or process having additional functionality not described in detail herein. Moreover, one or more of the tasks depicted in FIG. 5 could be omitted if the intended functionality is preserved.

As part of an initialization procedure, the coordinator device may perform testing to obtain measures of quality for one or more available wireless channels (task 502). The tested measure of quality may be associated with received signal strength, power, energy, or any measurable quantity. After testing the wireless channel quality, the coordinator device ranks the tested wireless channels based upon the measures of quality and generates an initial ordered list of the available wireless channels (task 504). In certain exemplary embodiments, the coordinator device scans and tests the available wireless channels in any order (random, predetermined, default, etc.) until it finds one that satisfies a threshold measure of quality, i.e., one that has less than a specified amount of channel noise/interference. At that point, process 500 need not continue testing additional channels, and the good channel is simply placed at or near the top of the ordered list. Any tested channels that do not satisfy the quality criteria will be placed at or near the bottom of the ordered list. In other exemplary embodiments, the coordinator device scans and tests all of the available wireless channels in any order, and then ranks all of those channels based upon their measured quality. In both embodiments, the ordered list is arranged in accordance with a quality measure of the available wireless channels, and the ordered list will include an entry for the first wireless channel to be utilized by the coordinator device. In this example, the initial wireless channel will be at the top of the ordered list, which indicates its ranking above the other available wireless channels. The initial ordered list of available wireless channels is saved and maintained at the coordinator device, which also sends the initial ordered list to the end node devices in the body area network (task 506). The initial ordered list is sent to the end node devices for reasons that will be explained below with reference to FIG. 6. The ordered list may be stored in, for example, the memory 312 of the coordinator device (see FIG. 3).

Eventually, the coordinator device selects the initial wireless channel for wireless communication with the end node devices in the body area network (task 508). The ellipses in FIG. 5 indicate that the initial tasks 502, 504, and 506 could be performed at any time prior to normal wireless operation of the system. During operation of the body area network, if the coordinator device detects quality degradation associated with the initial wireless channel or otherwise detects poor channel quality (query task 510), then it responds in an appropriate manner. For this embodiment, the coordinator device responds by testing a quality characteristic of the next wireless channel in the initial ordered list (task 512). The tested measure of quality may be associated with received signal strength, power, energy, or any measurable quantity. Task 512 serves as a double check or confirmation that the next wireless channel in the ordered list can actually be used under the current operating conditions. In the illustrated embodiment, a query task 514 checks for poor channel quality. Thus, if the obtained measure of quality does not satisfy a predetermined quality criteria for the wireless coordinator device (i.e., the coordinator device determines that the tested channel is of poor quality), then the process 500 repeats task 512 for the next channel in the initial ordered list. Thus, the process 500 will step through the initial ordered list until one of the available channels satisfies the quality criteria. If for some reason the coordinator device cannot find a good channel to use in place of the initial wireless channel, then the process 500 may exit without switching channels, or it may repeat the scanning procedure after a designated period of time has passed.

If the measured quality characteristic does not indicate poor channel quality (query task 514), then the coordinator device updates the ordered list of available wireless channels to indicate a higher preference for the new wireless channel, and to indicate a lower preference for the initial wireless channel (task 516). In certain embodiments, the initial wireless channel is rearranged in the updated ordered list such that it has the lowest preference (e.g., it now appears at the bottom of the updated ordered list). Moreover, the new wireless channel is identified for use as the current channel, and the new wireless channel appears at the top of the updated ordered list. The coordinator device sends the updated ordered list to the end node devices (task 518) for reasons that will be explained below with reference to FIG. 6. Eventually, the coordinator device switches from the initial wireless channel to the new wireless channel (task 520), and proceeds with wireless data communication (beacons, data packets, etc.) with the end node devices.

Notably, the updated ordered list replaces the initial ordered list, and the updated ordered list remains susceptible to further revision in an ongoing manner. In this regard, task 520 leads back to query task 510, which continues to monitor the quality of the current wireless channel. Thus, even though the body area network might change locations and positions, the ordered list of available channels can adapt as necessary to better reflect the relative preferences and quality of the different available channels.

Figure 6:
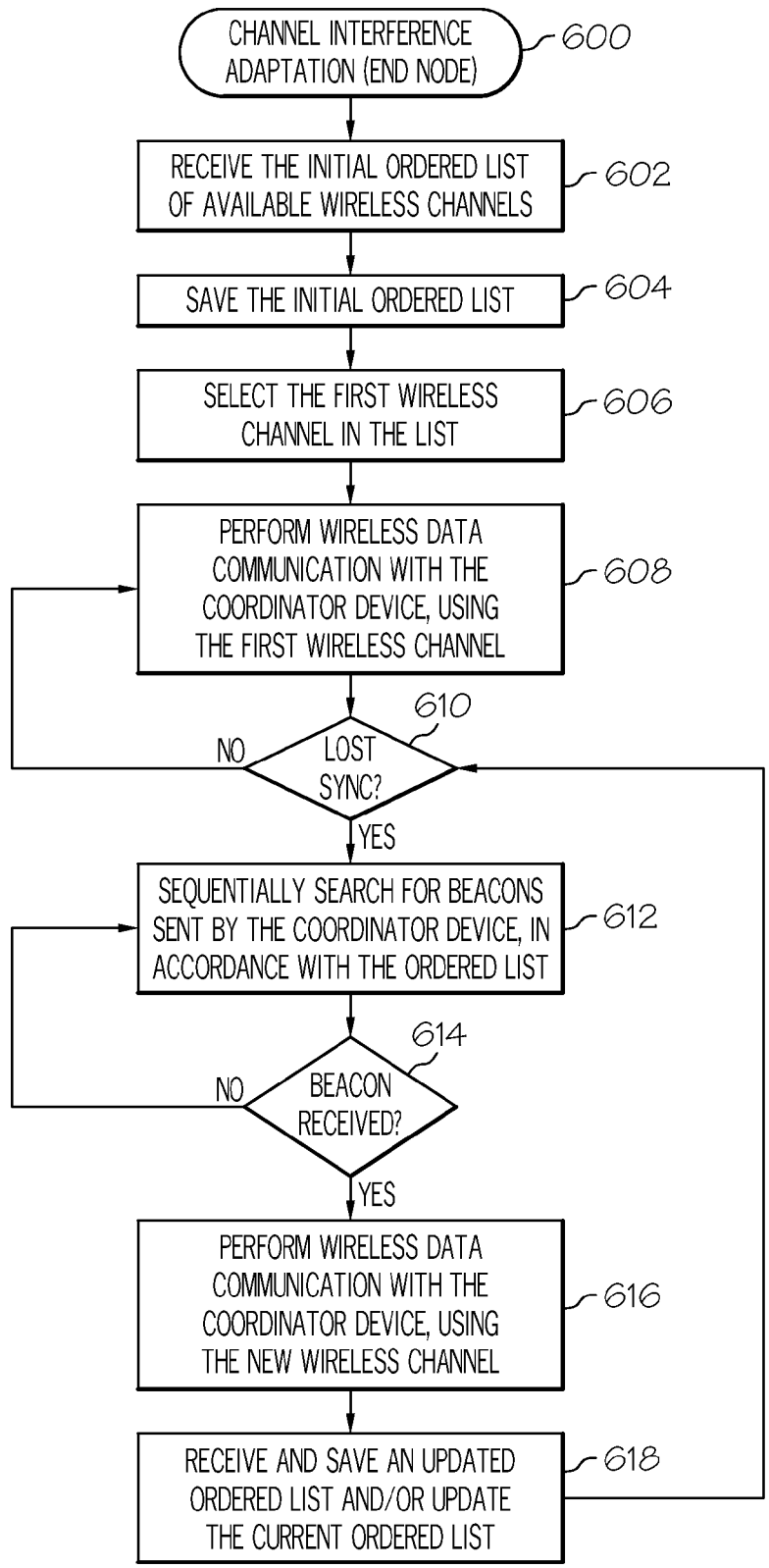
FIG. 6 is a flow chart that illustrates an exemplary embodiment of a channel interference adaptation process, which may be performed by a wireless end node device.

FIG. 6 is a flow chart that illustrates an exemplary embodiment of a channel interference adaptation process 600, which may be performed by a wireless end node device. The various tasks performed in connection with process 600 may be performed by software, hardware, firmware, or any combination thereof. For illustrative purposes, the following description of process 600 may refer to elements mentioned above in connection with FIGS. 1-3. It should be appreciated that process 600 may include any number of additional or alternative tasks, the tasks shown in FIG. 6 need not be performed in the illustrated order, and process 600 may be incorporated into a more comprehensive procedure or process having additional functionality not described in detail herein. Moreover, one or more of the tasks depicted in FIG. 6 could be omitted if the intended functionality is preserved.

The process 600 may begin by receiving, at the end node device, an initial ordered list of available wireless channels (task 602). The initial ordered list is saved and maintained by the end node device (task 604). As described above with reference to the process 500, the coordinator device transmits the initial ordered list to the end node devices after it completes the initial ranking of the wireless channels. The initial ordered list will include an entry for an initial wireless channel, which has been designated by the coordinator device as the currently active wireless channel for use with the end node device.

The end node device selects the first (initial) wireless channel in the ordered list, and uses that initial wireless channel to perform wireless data communication with the coordinator device (task 608). As explained previously, the end node device may receive beacons from the coordinator device, receive data packets from the coordinator device, transmit data packets to the coordinator device, and/or transmit pings to the coordinator device, using the initial wireless channel. During operation, however, the end node device may lose wireless connectivity with the coordinator device, or it may otherwise lose wireless synchronization with the coordinator device. Loss of synchronization may be caused by excessive channel noise, radiofrequency interference, excessive distance between the coordinator and end node device, deactivation or powering down of the coordinator device, or the like. If the end node device determines that wireless connectively with the coordinator device has been lost (query task 610), then it will search for wireless beacons sent by the coordinator device using one of the available channels, other than the initial wireless channel (task 612). In certain embodiments, task 612 sequentially searches and traverses the available wireless channels in accordance with the ordered list. Thus, upon loss of synchronization with the first wireless channel in the ordered list, the end node device will begin listening for beacons transmitted on the second wireless channel in the ordered list. As described above with reference to the process 500, the ordered list can be arranged according to a channel preference scheme that is known at the coordinator device. Thus, rather than randomly scanning the available channels, the end node device can quickly and intelligently begin its scan at the next preferred channel.

If the end node device does not receive a beacon using the second wireless channel in the ordered list (query task 614), then it will continue by listening for beacons on the third wireless channel in the ordered list. This routine may continue until the end node device receives a beacon on one of the alternate wireless channels. If for some reason the end node device does not receive a beacon on any alternate channel, other than the initial wireless channel, then the process 600 may exit without switching channels, or it may repeat the scanning procedure after a designated period of time has passed.

When the end node device receives a beacon on one of the available wireless channels (other than the initial wireless channel), it will switch to that new channel and use the new channel to perform wireless data communication with the coordinator device (task 616). This enables the end node device to continue receiving beacons from the coordinator device, receive data packets from the coordinator device, transmit data packets to the coordinator device, and/or transmit pings to the coordinator device, using the new wireless channel. After regaining wireless synchronization with the coordinator device, the end node device may receive an updated ordered list of available wireless channels from the coordinator device (task 618). This updated ordered list will be saved at the end node device for future reference. As mentioned above, the updated ordered list will indicate a higher preference for the new wireless channel and a lower preference for the initial wireless channel. Additionally (or alternatively), the end node device may initiate the updating of its current ordered list to reflect the changed status of both the new wireless channel (which now resides at the top of the ordered list) and the initial wireless channel (which now resides at the bottom of the ordered list).

Notably, the updated ordered list supersedes the initial ordered list, and the updated ordered list maintained at the end node device remains susceptible to further revision in an ongoing manner. In this regard, task 618 leads back to query task 610, which continues to monitor for loss of wireless synchronization associated with the current wireless channel. Thus, even though the body area network might change locations and positions, the ordered list of available channels can adapt as necessary to better reflect the relative preferences and quality of the different available channels. This enables the end node device to quickly react to wireless interruptions in an intelligent and efficient manner.

The channel interference adaptation techniques described here result in intelligent channel hopping in the presence of noise or interference. If the user travels to an unfamiliar location that happens to be RF noisy for the currently selected wireless channel, then the intelligent channel hopping scheme should choose a new channel that is preferred for that user. Conversely, the intelligent channel hopping scheme should not choose a new channel that has already been determined to be noisy in certain environments frequented by the user. Accordingly, when switching wireless channels, the body area network will be less likely to select a new channel that might be noisy in the user's home environment, work environment, school environment, etc. This aspect is beneficial for certain embodiments in which the newly selected wireless channel remains active (regardless of the location of the body area network) until RF noise, wireless interference, or loss of wireless synchronization is subsequently detected. Thus, as the body area network becomes exposed to different operating environments and wireless noise levels, the ordered list of wireless channels might dynamically change in a responsive manner.

In certain embodiments, the channel adaptation process and routines are automated and hidden from the user. In this regard, the user-specific channel ordering scheme (from good to bad) can be based on run-time behavior. Thus, if a particular channel was found to be bad from a prior channel-changing scenario, it will be moved to the bottom of the list in the background and with no user involvement. Likewise, if a particular channel is consistently found to be good (for the particular user), it will be moved closer to the top of the list. After weeks or months of usage, the system will have a channel list that has been dynamically ordered to be a preferred or optimized list for that user.

Location-Correlated Channel Management

A wireless medical device could also be suitably configured to support channel switching, selection, and/or user assignment based upon the geographic location or position of the wireless medical device. These location-correlated techniques could be used to supplement the wireless channel hopping scheme and/or the channel interference adaptation scheme described above. In this regard, the wireless medical device leverages some type of location-based service or technology to select a preferred channel for continued operation in the event of interference, poor channel quality, etc. The correlation of the location (geographic position) and the selected channel can be established, defined, or configured in a number of different ways. For example, the user could be given the option to mark which wireless channel they prefer for particular locations or areas (school, work, home, etc.), or the location-based channel assignment could be performed automatically by the wireless device itself based on wireless performance metrics. In practice, the wireless medical device or the user could assign a preferred channel to a location based on the frequency with which that particular channel has been used in that location, based on a measure of success using a particular channel in that location, or the like. During operation, the wireless medical device can automatically select the preferred channel, if needed, for a given area (assuming a preferred channel has already been assigned).

Figure 7:
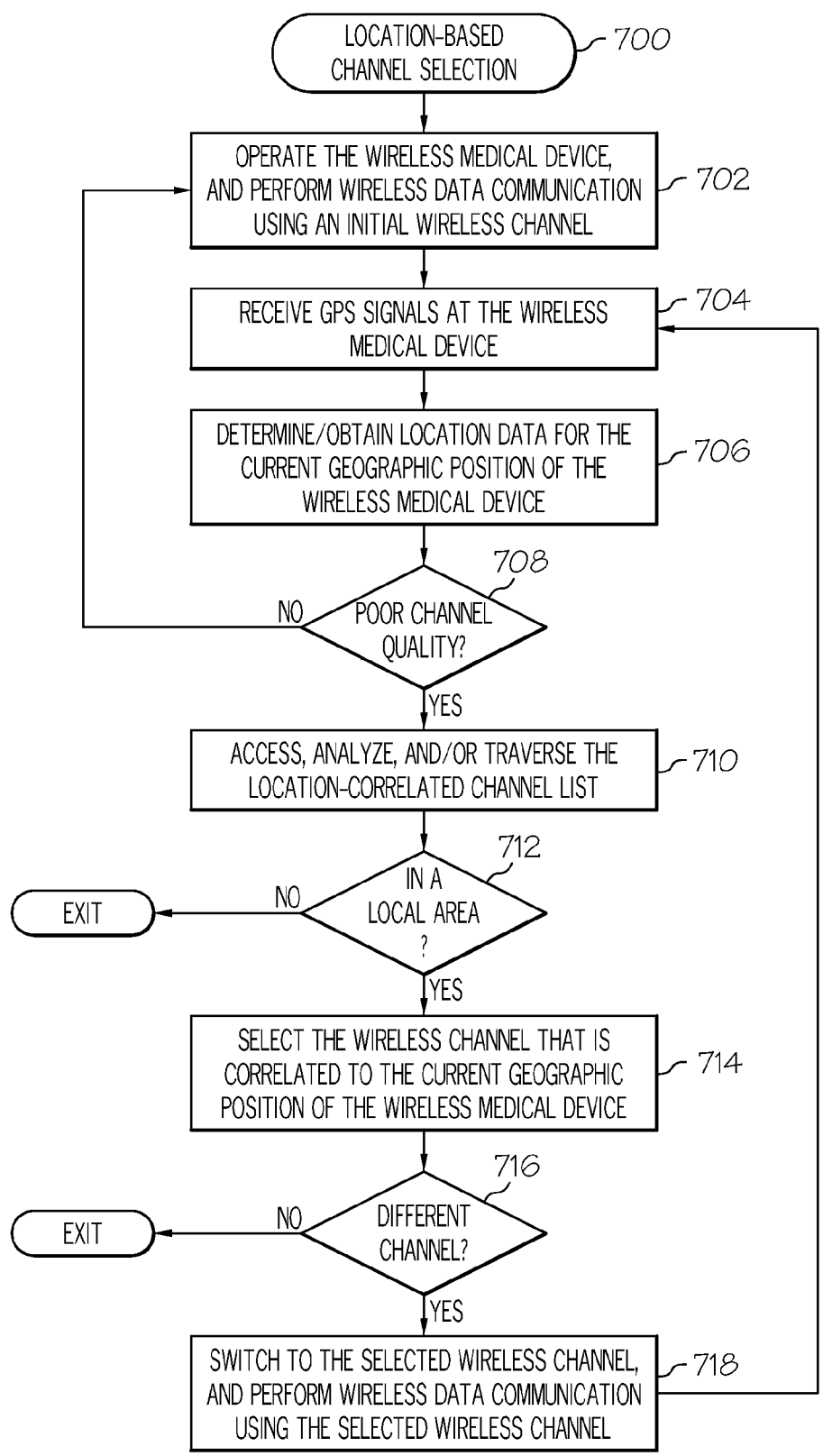
FIG. 7 is a flow chart that illustrates an exemplary embodiment of a location-based channel selection process, which may be performed by a wireless medical device.

FIG. 7 is a flow chart that illustrates an exemplary embodiment of a location-based channel selection process 700, which may be performed by a wireless medical device configured as described herein. The various tasks performed in connection with process 700 may be performed by software, hardware, firmware, or any combination thereof. For illustrative purposes, the following description of process 700 may refer to elements mentioned above in connection with FIGS. 1-3. It should be appreciated that process 700 may include any number of additional or alternative tasks, the tasks shown in FIG. 7 need not be performed in the illustrated order, and process 700 may be incorporated into a more comprehensive procedure or process having additional functionality not described in detail herein. Moreover, one or more of the tasks depicted in FIG. 7 could be omitted if the intended functionality is preserved.

The illustrated embodiment of process 700 begins by operating the wireless medical device (task 702). Operation of the wireless medical device may include performing wireless data communication using a first wireless channel (e.g., an initial channel) selected from a plurality of available wireless channels. This first wireless channel may be used to wirelessly communicate with another wireless device in the body area network. For this exemplary embodiment, the wireless medical device receives GPS signals during operation (task 704). The GPS signals are transmitted by GPS satellites and/or terrestrial GPS repeaters, as is well understood. Using its onboard GPS receiver capabilities, the wireless medical device can then process and analyze the received GPS signals to determine or obtain corresponding location data that is indicative of the current geographic position of the wireless medical device (task 706). In practice, task 706 might resolve the GPS coordinates for the current geographic position of the wireless medical device. It should be appreciated that tasks 704 and 706 are performed in the background in an ongoing manner such that the wireless medical device calculates and obtains its current geographic position in real-time, near-real-time, or as frequently as necessary. Moreover, as explained above with reference to FIG. 3, the wireless medical device could use a location-determining or a positioning technology other than GPS if so desired.

Although not required for all embodiments, the illustrated process 700 initiates channel selection and switching in the event of poor wireless channel quality, high wireless channel interference, low quality of service, or the like. In this regard, process 700 may trigger channel switching based upon a determination of poor channel quality (query task 708). Thus, if the wireless medical device automatically detects (or is informed of) quality degradation associated with the first wireless channel or otherwise detects poor channel quality, then process 700 continues to a task 710. If, however, the quality of the first wireless channel remains acceptable, then process 700 may exit or be re-entered at an appropriate point, such as task 702. It should be appreciated that query task 708 could be associated with a number of different triggering schemes, mechanisms, or routines. For example, poor channel quality may be automatically detected and acted upon by the wireless medical device with little to no user involvement. Alternatively, the determination of poor channel quality and/or the decision to change wireless channels may require at least some user interaction. In certain implementations, the user can manipulate the user interface of the wireless medical device to measure or view channel performance information and, if necessary or desired, command the wireless medical device to proceed with location-correlated channel selection.

In response to a determination that the first wireless channel is of poor quality (query task 708), task 710 accesses, analyzes, and/or traverses a location-correlated channel list (task 710) that is maintained at the wireless medical device. The location-correlated channel list includes a plurality of different entries, where each entry includes a designated wireless channel and a corresponding local area. Notably, a particular wireless channel (e.g., channel B) may be designated for a plurality of different local areas (e.g., a residence location and a school location). Moreover, a particular wireless channel that is available for use by the wireless medical device need not be assigned as a designated wireless channel for any local area. In exemplary embodiments, each local area contained in the list will (eventually) have a designated wireless channel assigned thereto. Although not always required, this exemplary and simple embodiment assumes that only one wireless channel can be designated for any one local area. However, it is also conceivable to have multiple channels assigned to a local area, each channel having similar performance metrics at the time the correlation with the location was made. The system could select one channel when entering a correlated location until such time that the selected channel no longer provides a "good" link. In this event the system could switch to a second location-correlated channel. For the exemplary system described here, the designated wireless channels represent preferred, optimized, desirable, or otherwise favored wireless channels. In this regard, a designated wireless channel (e.g., channel B) may represent a preferred wireless channel for a particular local area (e.g., the user's home), where that designated wireless channel satisfies predetermined quality criteria while the wireless medical device is located in that particular local area. Accordingly, the location-correlated list may be used to assign a respective wireless channel for operation of the wireless medical device in each local area of interest.

A "local area" as used in the context of this location-correlated channel management scheme could represent, indicate, include, or otherwise correspond to: a specific geographic location; a specific set of GPS coordinates; a defined range of GPS coordinates; an area or region within a specified radius of a particular geographic location; an area or region defined by the user; a predefined area or region, such as a zip code or an area code; or the like. These examples are not exhaustive, and a local area could be defined or indicated in other ways. In this regard, a local area might correspond to a location such as, and without limitation: a residence location (e.g., a house, an apartment complex, or a condominium unit); a workplace location; a school location (e.g., a classroom, a campus, or a building on a campus); a recreational location (e.g., a baseball stadium, a workout facility, or a skatepark); a business location (e.g., the user's place of work, a shopping mall, a grocery store, or a corporate campus); etc. Moreover, the range covered by a given local area can start out small, but then automatically be extended to additional adjoining location coordinates if the channel quality is assessed to be good. For example, the user's house may be initially designated as a local area that has been correlated with a channel. If the user leaves the house and walks around the neighborhood, the system could continue to correlate and assign new location coordinates to the same channel if the signal quality remains good.

Referring again to FIG. 7, process 700 reviews the location-correlated channel list to determine, from the current location data, whether or not the wireless medical device is now located in one of the local areas contained in the channel list (query task 712). In practice, task 712 may be associated with a comparison routine that compares the current location data to stored location data associated with the local areas included in the channel list. For instance, task 712 could check whether the current location data indicates that the wireless medical device is within a predetermined radius (e.g., 100 feet, 50 yards, 75 feet) of a saved geographic position, or whether the current location data indicates that the wireless medical device is located within the boundaries of a saved building, campus, or other defined region.

If query task 712 determines that the wireless medical device is not located in one of the specified local areas, then process 700 may exit or be re-entered at an appropriate point. In certain embodiments, process 700 could exit at this point and initiate other channel hopping or selection techniques (such as those described in more detail above). If query task 712 determines that the wireless medical device is currently located in a listed local area, then the wireless medical device can identify and select the wireless channel that is correlated to that listed local area (task 714). Thus, the selected wireless channel will also be correlated to the current location data and, in turn, correlated to the current geographic position of the wireless medical device. Process 700 may then check whether the newly selected wireless channel is different than the current wireless channel (query task 716). If the newly selected wireless channel is not different than the current wireless channel, then process 700 may exit or be re-entered at an appropriate point. In certain embodiments, process 700 could exit at this point and initiate other channel hopping or selection techniques (such as those described in more detail above).

If, however, the newly selected wireless channel is a different channel, then the wireless medical device switches to the newly selected wireless channel and performs wireless data communication using the new channel (task 718). In other words, process 700 will cause the wireless medical device to proceed with wireless data communication using the preferred wireless channel that had been previously designated for the local area in which the wireless medical device now resides. FIG. 7 depicts task 718 leading back to task 704 because the location-based channel selection process 700 is dynamic and ongoing in nature. Thus, process 700 continues to monitor the current geographic position of the wireless medical device, check the quality of the currently selected wireless channel, and make location-based changes to the wireless channel if necessary.

Figure 8:
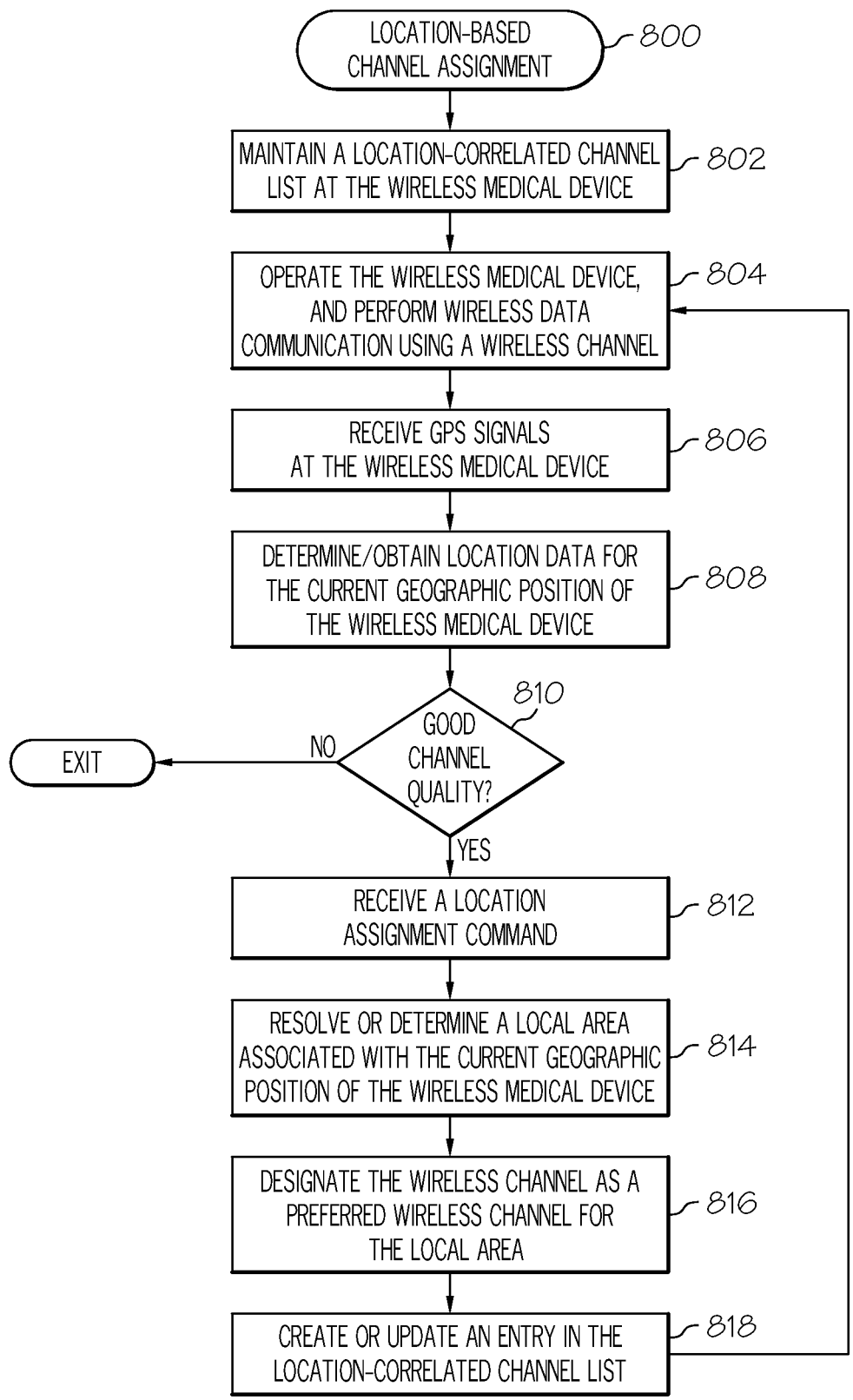
FIG. 8 is a flow chart that illustrates an exemplary embodiment of a location-based channel process, which may be performed by a wireless medical device.

As mentioned above, the wireless medical device can maintain, store, and update a suitable location-correlated channel list for purposes of the location-based channel selection scheme. In practice, this channel list could be generated, modified, and updated in a dynamic manner as needed for user customization. In this regard, FIG. 8 is a flow chart that illustrates an exemplary embodiment of a location-based channel process 800, which may be performed by a wireless medical device configured as described herein. The various tasks performed in connection with process 800 may be performed by software, hardware, firmware, or any combination thereof. For illustrative purposes, the following description of process 800 may refer to elements mentioned above in connection with FIGS. 1-3. It should be appreciated that process 800 may include any number of additional or alternative tasks, the tasks shown in FIG. 8 need not be performed in the illustrated order, and process 800 may be incorporated into a more comprehensive procedure or process having additional functionality not described in detail herein. Moreover, one or more of the tasks depicted in FIG. 8 could be omitted if the intended functionality is preserved.

The illustrated embodiment of process 800 begins by creating, generating, or maintaining the location-correlated channel list at the wireless medical device (task 802). When the wireless medical device is initially deployed "out of the box" this channel list might be empty and ready to populate, or it may not even exist. If it doesn't exist, then the user could be prompted to create the channel list at an appropriate time. The process could also automatically, without user interaction, initiate the population of location-based data and corresponding correlation with the channel in use having been selected as an initial choice or through channel hopping as described further herein. At a suitable time, the process would inform the user that it has correlated a channel with a location and prompt the user for further action such as storing the data.

The remainder of process 800 assumes that the channel list (which may be empty, partially completed, or fully completed) has already been created and is being maintained by the wireless medical device.

Process 800 may continue by operating the wireless medical device (task 804). Operation of the wireless medical device may include performing wireless data communication using a first wireless channel (e.g., an initial channel) selected from a plurality of available wireless channels. In this regard, task 804 is similar to task 702 described above for process 700. For this exemplary embodiment, the wireless medical device receives GPS signals during operation (task 806), and determines or obtains corresponding location data that is indicative of the current geographic position of the wireless medical device (task 808). These tasks are similar to tasks 704 and 706 described above for process 700 and, therefore, will not be redundantly described here.

Although not required for all embodiments, the illustrated process 800 allows the user to choose or identify "good" or "preferred" wireless channels and assign those channels to geographic regions, local areas, familiar places, etc. Accordingly, process 800 may check for, and provide the user with a measure or indication of, good wireless channel quality (query task 810). Thus, if the wireless medical device detects (or is informed of) low interference, high quality of service, and/or other metrics indicative of good quality associated with the current wireless channel, then process 800 continues to a task 812. If, however, the quality of the current wireless channel is unacceptable or otherwise does not satisfy certain performance criteria, then process 800 may exit or be re-entered at an appropriate point, such as task 804.

This example assumes that the process 800 can respond to a user request or command to assign the "good" wireless channel to the current geographic position of the wireless medical device. This enables the medical device to dynamically populate, update, and/or modify at least a portion of its location-correlated channel list during operation. In this regard, the wireless medical device could receive an appropriately formatted location assignment command or instruction (task 812), which may be initiated by the user. For example, the user interface of the wireless medical device could present instructions or a menu item to the user, which prompts the user to assign the current wireless channel to a particular region, area, location, or the like. The user could select a "save channel" option or otherwise cause the wireless medical device to proceed with the location-based channel assignment procedure.

In response to the location assignment command, process 800 may resolve or determine a local area, a region, a boundary, and/or a defined geographic sector that is associated with the current geographic position of the wireless medical device (task 814). The defined local area may include the precise geographic position (as indicated by the GPS coordinates) of the wireless medical device, in addition to a predefined boundary radius, as explained above with reference to the process 700. Alternatively, the local area could be defined or determined using other boundaries, geographic markers, or the like. Process 800 may also designate the current wireless channel as a preferred wireless channel for the determined local area (task 816), and then save the correlated relationship between that wireless channel and the determined local area. For this embodiment, the wireless medical device creates or updates an entry in the location-correlated channel list (task 818) to reflect this new channel assignment.

FIG. 8 depicts task 818 leading back to task 804 because the location-based channel assignment process 800 can be performed in a dynamic and ongoing manner. Thus, process 800 may continue to monitor the current geographic position of the wireless medical device, check the quality of the wireless channel, and allow additional location-based channel assignments for one or more other local areas. Indeed, any number of iterations of process 800 could be performed to contemplate any number of different local areas, or compare current channel quality data with previous data as the presence of interfering signals resulting in poor link quality could conceivably change over time. Again, the location-correlated channel list can be accessed during operation of the wireless medical device, as described above for the process 700.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of operating a wireless coordinator device in a wireless local insulin infusion system comprising a body area network of wireless medical devices, the method comprising:

detecting loss of wireless synchronization, for a current wireless data communication channel, between the wireless coordinator device and a wireless glucose sensor transmitter device of the wireless local insulin infusion system, wherein detecting loss of wireless synchronization comprises determining that the wireless coordinator device missed at least a threshold number of expected wireless pings in sequence from the wireless end node device, wherein wireless pings are sent from the wireless glucose sensor transmitter device using the current wireless data communication channel, wherein the wireless pings are sent from the wireless glucose sensor transmitter device according to a transmit schedule of which both the wireless glucose sensor transmitter device and the wireless coordinator device are aware, and wherein each wireless ping is a glucose data packet that conveys glucose data when glucose sensor data is available, or a dummy packet that conveys no data when glucose sensor data is unavailable;

in response to detecting loss of wireless synchronization, obtaining a measure of quality for the current wireless data communication channel;

when the obtained measure of quality fails to satisfy a threshold criteria, selecting a new wireless data communication channel for the wireless coordinator device; and thereafter, transmitting wireless beacons with the wireless coordinator device, using the new wireless data communication channel.

2. The method of claim 1, further comprising obtaining, for a plurality of available wireless data communication channels, a respective measure of wireless channel quality, wherein the new wireless data communication channel is selected from the plurality of available wireless data communication channels based upon its respective measure of wireless channel quality.

3. The method of claim 2, wherein the respective measure of wireless channel quality for the new wireless data communication channel indicates highest quality among the plurality of available wireless data communication channels.

4. The method of claim 1, further comprising:
prior to detecting loss of wireless synchronization, sending initial wireless beacons from the wireless coordinator device, using the current wireless data communication channel; and
prior to obtaining the measure of quality for the current wireless data communication channel, ceasing the sending of the initial wireless beacons.

5. The method of claim 1, further comprising:
saving, at the wireless coordinator device, ping timing information corresponding to the wireless glucose sensor transmitter device; and
synchronizing the wireless coordinator device for receipt of wireless pings from the wireless glucose sensor transmitter device in accordance with the saved ping timing information, wherein detecting loss of wireless synchronization utilizes the saved ping timing information.

6. The method of claim 5, further comprising receiving the ping timing information from the wireless glucose sensor transmitter device.

7. A method of operating a wireless coordinator device in a wireless local insulin infusion system that includes a wireless glucose sensor transmitter device, the method comprising:
obtaining, at the wireless coordinator device, a ping schedule for the wireless glucose sensor transmitter device, the ping schedule indicating time slots during which the wireless coordinator device should expect to receive pings from the wireless glucose sensor transmitter device, wherein each ping is a glucose data packet that conveys glucose data when glucose sensor data is available, or a dummy packet that conveys no data when glucose sensor data is unavailable;
configuring the wireless coordinator device to monitor for pings sent by the wireless glucose sensor transmitter device in accordance with the ping schedule;
the wireless coordinator device performing wireless data communication with the wireless glucose sensor transmitter device, using a current wireless data communication channel;
detecting that the wireless coordinator device missed at least a threshold number of expected wireless pings in sequence as indicated by the ping schedule, the wireless pings sent from the wireless glucose sensor transmitter device using the current wireless data communication channel;
in response to the detecting step, testing quality of the current wireless data communication channel;
when the quality of the current wireless data communication channel is below a threshold quality measure, selecting a new wireless data communication channel; and
thereafter, the wireless coordinator device using the new wireless data communication channel to transmit wireless beacons and to receive wireless pings from the wireless glucose sensor transmitter device.

8. The method of claim 7, further comprising obtaining, for a plurality of available wireless data communication channels including the new wireless data communication channel, a respective measure of wireless channel quality, wherein the new wireless data communication channel is selected from the plurality of available wireless data communication channels based upon its respective measure of wireless channel quality.

9. The method of claim 7, further comprising:
obtaining, at the wireless coordinator device, a second ping schedule for a wireless end node device operating in the wireless local insulin infusion system, the second ping schedule indicating time slots during which the wireless coordinator device should expect to receive pings from the wireless end node device;
configuring the wireless coordinator device to monitor for pings sent by the wireless end node device in accordance with the second ping schedule; and
the wireless coordinator device performing wireless data communication with the wireless end node device, using the current wireless data communication channel.

10. A wireless medical device for a wireless local insulin infusion system comprising a body area network of medical devices, the wireless medical device comprising:
a processor;
a memory element coupled to the processor and configured to store a ping schedule for a wireless glucose sensor transmitter device; and
a wireless communication module coupled to the processor and configured to receive ping messages from the wireless glucose sensor transmitter device using a current wireless data communication channel, wherein each wireless ping message is a glucose data packet that conveys glucose data when glucose sensor data is available, or a dummy packet that conveys no data when glucose sensor data is unavailable;
wherein the processor is configured to:
detect when the wireless communication module has missed at least a threshold number of expected ping messages in sequence from the wireless glucose sensor transmitter device, as indicated by the ping schedule;
test a quality characteristic of the current wireless data communication channel when the wireless communication module has missed at least the threshold number of expected ping messages in sequence; and
switch from the current wireless data communication channel to a new wireless data communication channel when the quality characteristic fails to satisfy predetermined quality criteria.

11. The wireless medical device of claim 10, wherein the wireless communication module is configured to transmit wireless beacons using the new wireless data communication channel.

12. The wireless medical device of claim 10, wherein the processor is configured to obtain, for a plurality of available wireless data communication channels including the new wireless data communication channel, a respective measure of wireless channel quality, and is further configured to select the new wireless data communication channel from the plurality of available wireless data communication channels based upon its respective measure of wireless channel quality.

13. The wireless medical device of claim 10, wherein the wireless communication module is configured to receive the ping schedule from the wireless glucose sensor transmitter device.

* * * * *